(12) United States Patent
Lippe et al.

(10) Patent No.: US 9,650,681 B2
(45) Date of Patent: May 16, 2017

(54) METHODS FOR THE DETECTION AND IDENTIFICATION OF EXTENDED SPECTRUM BETA LACTAMASES

(75) Inventors: Catherine Lippe, Quebec (CA); Isabelle Duteaud, Quebec (CA); Celine Roger-Dalbert, Quebec (CA)

(73) Assignee: GENEOHM SCIENCES, INC., San Diego, CA (US)

( * ) Notice: Subject to any disclaimer, the term of this patent is extended or adjusted under 35 U.S.C. 154(b) by 0 days.

(21) Appl. No.: 13/213,010

(22) Filed: Aug. 18, 2011

(65) Prior Publication Data

US 2012/0070828 A1  Mar. 22, 2012

Related U.S. Application Data

(63) Continuation of application No. PCT/US2010/024832, filed on Feb. 19, 2010.

(60) Provisional application No. 61/153,954, filed on Feb. 19, 2009.

(51) Int. Cl.
*C12P 19/34* (2006.01)
*C12Q 1/68* (2006.01)

(52) U.S. Cl.
CPC ....... *C12Q 1/689* (2013.01); *C12Q 2600/156* (2013.01)

(58) Field of Classification Search
USPC ............................ 435/6.12, 91.2
See application file for complete search history.

(56) References Cited

U.S. PATENT DOCUMENTS

| | | |
|---|---|---|
| 4,458,066 A | 7/1984 | Caruthers et al. |
| 5,475,610 A | 12/1995 | Atwood et al. |
| 5,538,871 A | 7/1996 | Nuovo et al. |
| 5,602,756 A | 2/1997 | Atwood et al. |
| 5,612,473 A | 3/1997 | Wu et al. |
| 5,780,610 A | 7/1998 | Collins et al. |
| 2007/0248954 A1 | 10/2007 | Hanson |

FOREIGN PATENT DOCUMENTS

| | | |
|---|---|---|
| JP | 2007-504829 A | 4/2007 |
| WO | WO 2005/024045 A2 | 3/2005 |
| WO | WO 2008/124670 | 10/2008 |

OTHER PUBLICATIONS

Birkett et al. (2007) J. of Medical Microbiol. vol. 56: 52-55.*
Stratagene 1988 catalog.*
Cole et al. J. of clinical Microbiol. 2009 vol. 47: No. 2: pp. 322-326 (Nov. 26, 2008 online publication date) doi:10.1128/JCM.01550-08.*
Ensor et al. (Jan. 25, 2007 online publication) J. of Antimicrobial Chemotherapy vol. 59, 387-395.*
You et al. (May 2, 2006 online publication date) Nucleic Acids Res. vol. 34 No. 8 e60 doi:10.1093/nar/gk1175.*
Beaucage et al., Deoxynucleoside phosphoramidites—A new class of key intermediates for Deoxypolynucleotide synthesis. Tetrahedron Letters (1981) 22(20): 1859-1862.
Birkett et al., Real-time TaqMan PCR for rapid detection and typing of genes encoding CTX-M extended-spectrum β-lactamases. J Med Microbio. (Jan. 2007) 56(Pt 1): 52-55.
Bonnet et al., Growing group of extended-spectrum beta-lactamases: the CTX-M enzymes. Antimicrob. Agents Chemother. (Jan. 2004) 48(1):1-14.
Braasch et al., , Locked nucleic acid (LNA); fine-tuning the recognition of DNA and RNA. Chemistry & Biology (Jan. 2001) 8(1): 1-7.
Brown et al. Chemical synthesis and cloning of a tyrosine tRNA gene. Methods in Enzymology (1979) 68:109-151.
Dieffenbach et al. (Eds.) PCR Primer: A Laboratory Manual. (2003) CSHL Press, [Table of Contents only].
Govinden et al., Geographical evolution of the CTX-M β-lactamase—an update. Afr J Biotechnol. (Apr. 2007) 6(7):831-839.
Koh et al., Klebsiella pneumoniae strain EU2673 CTX-Mbeta-Lactamase gene, partial cds, GenBank AY517476.1, Submitted Jan. 2, 2004, retrieved online http://www.ncbi.nlm.nih.gov/nuccore/AY517476.1, 1 page.
Lartigue et al., Diversity of genetic environment of $bla_{CTX-M}$ genes. FEMS Microbio Lttrs. (May 2004) 234(2): 201-207.
Leach et al. Theoretical investigations of novel nucleic acid bases. J. Am. Chem. Soc. (1992) 114: 3675-3683.
Mantsch et al. Structural and Enzymatic Properties of Adenine I-Oxide Nucleotides. Biochem. (1993) 14(26):5593-5601.
McPherson et al. (Eds.) PCR: A Practical Approach, (c) 1991, Oxford University Press, Oxford, England, [Table of Contents Only].
Murray et al. (Eds.) Manual of Clinical Microbiology, 8th edition, ASM Press, Washington D.C. (2003). [Table of Contents only].
Naas et al., Minor extended-spectrum β-lactamases. Clin Microbiol Infect. (Jan. 2008) 14(Supll 1): 42-52.
Narang et al. Improved phosphotriester method for the synthesis of gene fragments. Methods Enzymol. (1979) 68:90-98.
Persing et al. (Eds.) Diagnostic Molecular Microbiology: Principles and Applications. American Society for Microbiology, Washington, D.C. (1993). [Table of Contents only].
Pitout et al., Phenotypic and molecular detection of CTX-M-β-Lactamases produced by *Escherichia coli* and *Klebsiella* spp. J Clin Microbiol. (Dec. 2004) 42(12): 5175-5721.
Pitout et al., Development and clinical validation of a molecular diagnostic assay to detect CTX-M-type β-lactamases in Enterobacteriaceae. Clin Microbiol Infect. (Mar. 2007) 13(3): 291-297.

(Continued)

*Primary Examiner* — Kenneth Horlick
(74) *Attorney, Agent, or Firm* — Knobbe, Martens, Olson and Bear, LLP

(57) ABSTRACT

Embodiments disclosed herein relate to compositions for the detection and/or identification of microbes that carry extended spectrum beta-lactamase genes. Specifically, provided herein are oligonucleotides, probes, and kits containing the same, for the detection of bacterial CTX-M sequences. Also provided are methods for the detection and/or amplification of microbes harboring extended spectrum beta-lactamase genes, including CTX-M type extended spectrum beta-lactamase genes.

24 Claims, 20 Drawing Sheets

(56) References Cited

OTHER PUBLICATIONS

Rossolini et al., The spread of CTX-M-type extended-spectrum beta-lactamases. Clin Microbiol Infect. (2008) 14(Suppl 1): 33-41 & Erratum.
Sambrook et al., (Eds.) Molecular Cloning: A Laboratory Manual, New York: Cold Spring Harbor Press (1989). [Table of Contents only].
Shahid, *Escherichia coli* strain MS INC03 beta-lactamase (blaCTX-M-15) gene, partial cds, GenBank EF371800.1, Submitted Jan. 17, 2007, retrieved online http:www.ncbi.nlm.nih.gov/nuccore/EF371800.1, 1 page.
Switzer et al. Enzymatic recognition of the base pair between isocytidine and isoguanosine. Biochemistry (1993) 32(39):10489-10496.
Tor et al., Site-specific enzymatic incorporation of an unnatural base . . . J. Am. Chem. Soc. (1993) 115:4461-4467.
Urban et al., Carbapenem-resistant *Escherichia coli* harboring Klebsiella pneumoniae carbapenemase β-lactamases associated with long-term care facilities. Clin Infect Dis. (Jan. 2008) 46(11):e127-130.
Walther-Rasmussen et al., Cefotaximases (CTX-M-ases), an expanding family of extended- spectrum β-lactamases. Can J Microbiol. (2004) 50(3):137-165.
Woodford et al. Outbreak of *Klebsiella pneumoniae*Producing a New Carbapenem-Hydrolyzing Class A β-Lactamase, KPC-3, in a New York Medical Center. Antimicrob. Agents Chemother (2004) 48(12) : 4793-4799.
Yigit et al. Novel Carbapenem-Hydrolyzing β-Lactamase, KPC-1, from a Carbapenem-Resistant Strain of *Klebsiella pneumoniae*. Antimicrob. Agents Chemother (Apr. 2001) 45(4): 1151-1161 & Erratum.
International Search Report and Written Opinion dated Jun. 9, 2010 for PCT/US10/24832, filed Feb. 19, 2010.
International Preliminary Report on Patentability dated Aug. 23, 2011 for PCT/US10/24832, filed Feb. 19, 2010.
Markowska et al., CTX-M-3 extended-spectrum β-lactamase-producing *Klebsiella pneumoniae* and dissemination of the plasmidic $bla_{CTX-M-3}$ in Bulgaria. Eur J Clin Microbiol Infect Dis. (2006) 25: 123-125.
Metan et al., CTX-M-3-type extended-spectrum β-lactamase-producing *Morganella morganii*: first description of an isolate from Turkey. Int J Antimicrob Agts. (2007) 30(4): 368-370.
Naas et al., Identification of CTX-M-Type Extended-spectrum-β-Lactamase Genes using Real-time PCR and Pyrosequencing. Antimicro Agts Chemother. (2006) 51(1): 223-230.
Oxacelay et al., P572 Identification of CTX-M-type extended-spectrum β-lactamases in urine based on real-time PCT. Int. J Antimicrob Agts. (2007) 29: S130/131.
Park et al., Co-production of 16S rRNA methylases and extended-spectrum β-lactamases in AmpC-producing *Enerobacter cloacae, Citrobacter freundii* and *Serratia marcescens* in Korea. J Antimicro Chemother. (2006) 58(4): 907-908.
Weill et al., Characterization of extended-spectrum-β-lactamase (CTX-M-15)-producing strains of *Salmonella enterica* isolated in france and Senegal. FEMS Microbio Lttrs. (2004) 238(2): 252-258.
Wu et al., Prevalence of extended-spectrum β-lactamases in *Proteus mirabilis* in a Taiwanese university hospital, 1999 to 2005: identification of a novel CTX-M enzyme (CTX-M-66). Diag Micro Infect Dis. (2008) 60(2): 169-175.
Xiong et al., Detection of CTX-M-14 extended-spectrum β-lactamase in *Shigella sonnei* isolates from China. J Infect. (2007) 55(5): E125-E128.
European Search Report dated Jul. 6, 2012 for European Application No. 10744408.5, filed Feb. 19, 2010.
Chinese Office Action dated Feb. 28, 2013 for Chinese Application No. CN102388150-A, filed Feb. 19, 2010.
Australian Patent Examination Report dated Mar. 6, 2014 for Application No. 2010215827, filed Feb. 19, 2010.
Chinese Office Action dated Sep. 30, 2014 for Application No. 2010800151567, filed Feb. 19, 2010.
Japanese Office Action dated Jul. 1, 2014 for Application No. 2011-551261, filed Feb. 19, 2010.
Canadian Office Action dated Feb. 16, 2016 for Application No. 2752913, filed Feb. 19, 2010.

\* cited by examiner

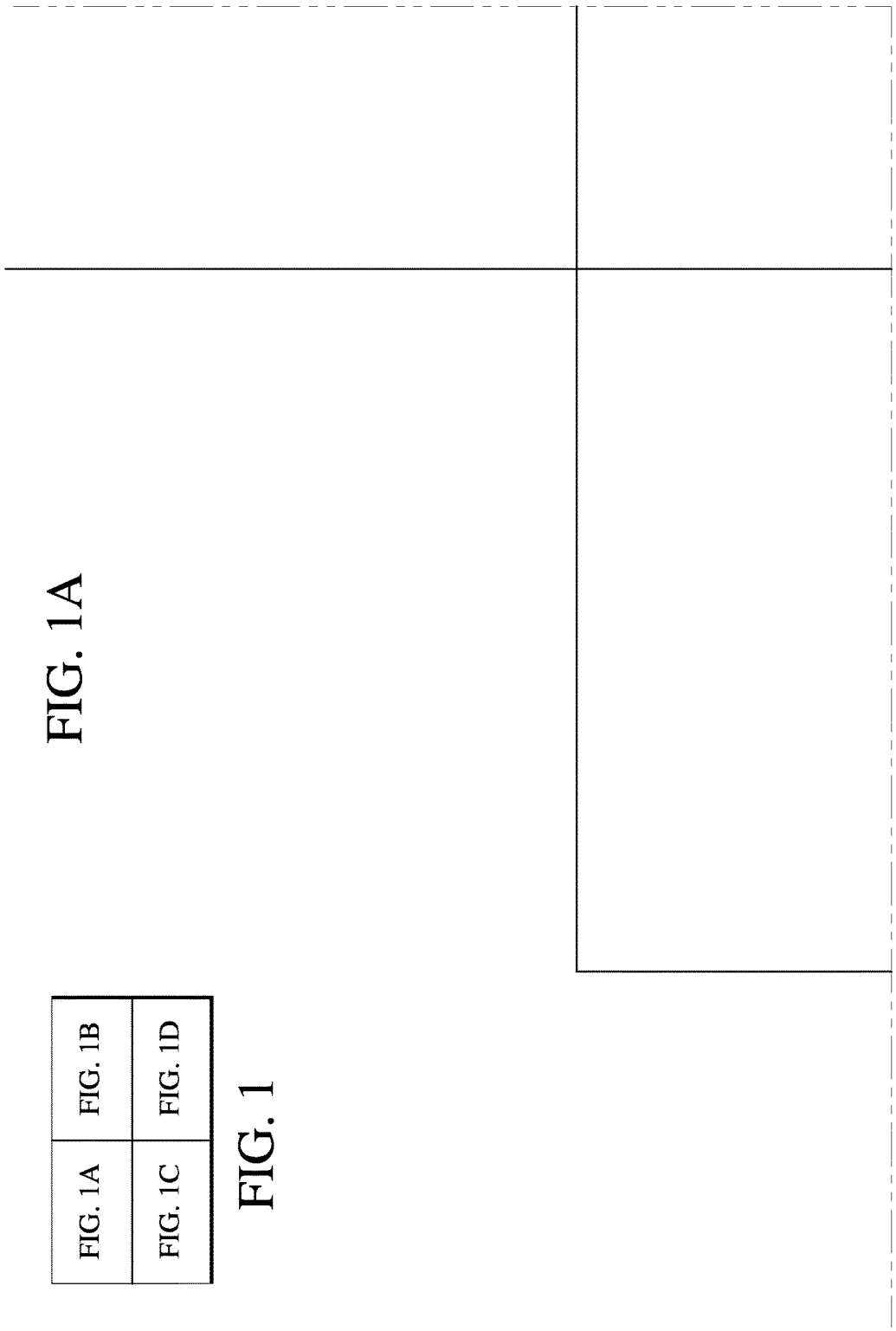

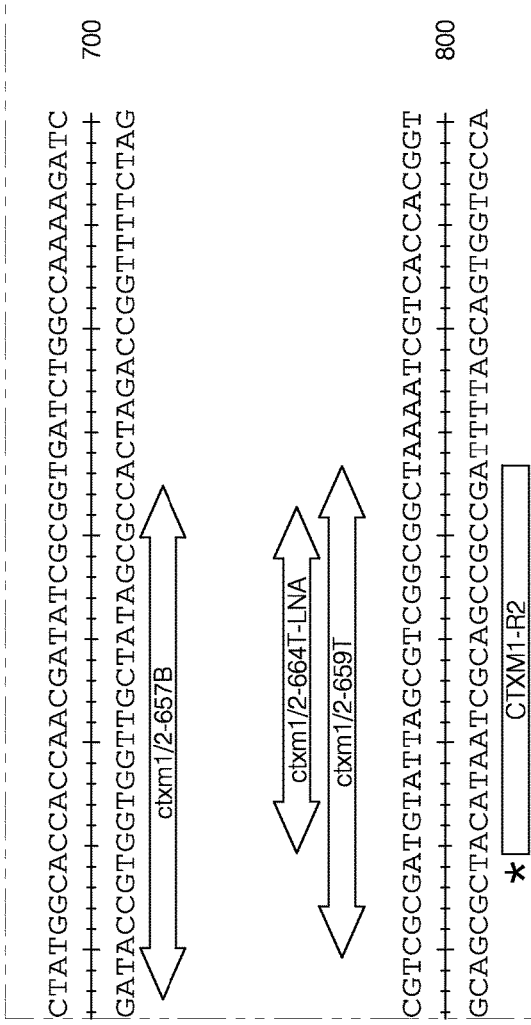

FIG. 3C

```
5'  TTCGGGCGGGTCTGCCGAAATCATGGGTAGTGGGCGATAAAACCGGCAGCGAGAT
    ||||||||||||||||||||||||||||||||||||||||||||||||||||||
3'  AAGCCCGCCCAGAGACGGCTTTAGTACCCATCACCGCTATTTGGCCGTCGCCTCTA
         ctxm...90F        ctxm2-609F 5'  CGCACCGCTGGTTCTGGTGACCTACTTTACCCAACCGGAGCAGAAGGCGAAAGCC
    ||||||||||||||||||||||||||||||||||||||||||||||||||||||
3'  GCGTGGCGACCAAGACCACTGGATGAAATGGGTTGGCCTCGTCTTCCGCCTTTCGG
                                  ctxm2-624F 5'  TTCTGA
    ||||||
3'  AAGACT              ctxm2-759R
```

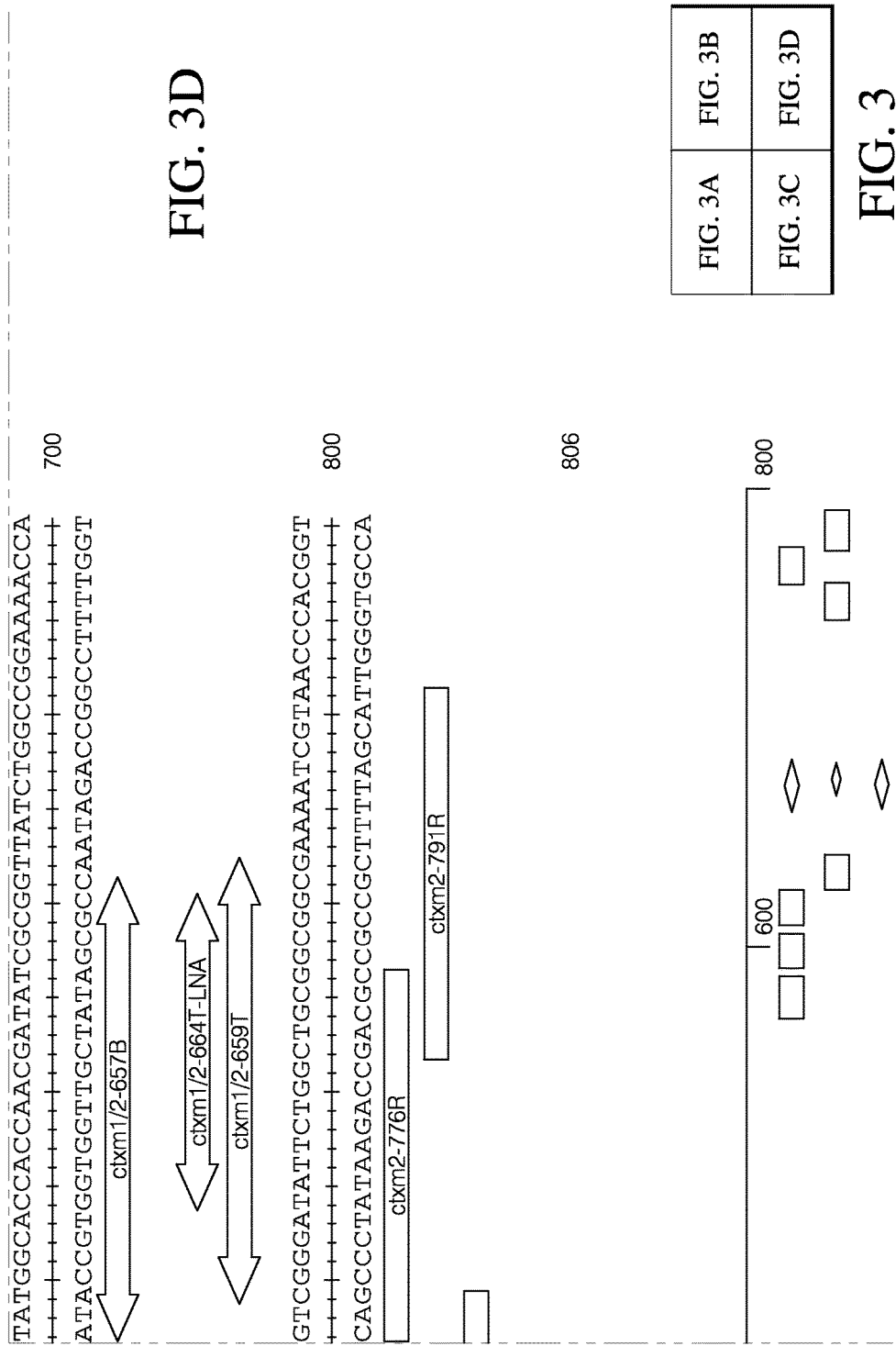

```
5'  CAGGCTCTGCGCAATCTGACGTTGGGCAATGCCCTGGGTGACACTCAGCGTGCGCA
    ||||||||||||||||||||||||||||||||||||||||||||||||||||||||
3'  GTCCGAGACGCGTTAGACTGCAACCCGTTACGGGACCCACTGTGAGTCGCACGCGT

5'  TTCAGGCAGGGCTACCCACATCGTGGGTTGTCGGGATAAAACCGGCAGCGGCGAT
    ||||||||||||||||||||||||||||||||||||||||||||||||||||||
3'  AAGTCCGTCCCGATGGGTGTAGCACCCAACAGCCCCTATTTTGGCCGTCGCCGCTA

5'  CGCGCCGCTCGTTCTGGTGACTTACTTCACCCAGTCGGAGCCGAAGGCAGAGAGCC
    |||||||||||||||||||||||||||||||||||||||||||||||||||||||
3'  GCGCGGCGAGCAAGACCACTGAATGAAGTGGGTCAGCCTCGGCTTCCGTCTCTCGG

5'  TATTAA
    ||||||
3'  ATAATT
```

FIG. 4C

```
GCTGGTGATGTGGCTGAAAGGCAACACCACCGGCGCTGCCAGCA
     ----+----+----+----+----+----+----+----+---- 600
CGACCACTACACCGACTTTCCGTTGTGGTGGCCGCGACGGTCGT

TATGGTACGACGAATGATATCGCGGTTATTTGGCCGGAAGGTCG
     ----+----+----+----+----+----+----+----+---- 700
ATACCATGCTGCTTACTATAGCGCCAATAAACCGGCCTTCCAGC

GTCGTGACGTGCTCGCTGCTGCCGCCCAGAATTGTCACCGACGGT
     ----+----+----+----+----+----+----+----+---- 800
CAGCACTGCACGAGCGACGACGGGGTCTTAACAGTGGCTGCCA
                                              806
```

FIG. 4D

| FIG. 4A | FIG. 4B |
| --- | --- |
| FIG. 4C | FIG. 4D |

FIG. 4

```
5'   CAGACGTTGCGTCAGCTTACGCTGGGTCATGCGCTGGGCGAAACCCAGCGGGCGCA
     ||||||||||||||||||||||||||||||||||||||||||||||||||||||||
3'   GTCTGCAACGCAGTCGAATGCGACCCAGTACGCGACCCGCTTTGGGTCGCCCGCGT
         *    [ CTXM914R ]

5'   TTCGGGCCGGCTTACCGACGTCGTGGACTGTGGGTGATAAGACCGGCAGCGGCGAC
     ||||||||||||||||||||||||||||||||||||||||||||||||||||||||
3'   AAGCCCGGCCGAATGGCTGCAGCACCTGACACCCACTATTCTGGCCGTCGCCGCTG

5'   TGCGCCGCTGGTTCTGGTGACCTATTTTACCCAGCCGCAACAGAACGCAGAGAGCC
     ||||||||||||||||||||||||||||||||||||||||||||||||||||||||
3'   ACGCGGCGACCAAGACCACTGGATAAAATGGGTCGGCGTTGTCTTGCGTCTCTCGG

5'   CTGTAA
     ||||||
3'   GACATT
```

FIG. 5C

```
GTTGGTGACGTGGCTCAAAGGCAATACGACCGGCGCAGCCAGCA
                                              600
CAACCACTGCACCGAGTTTCCGTTATGCTGGCCGCGTCGGTCGT

TACGGCACCACCAATGATATTGCGGTGATCTGGCCCAGGGTCG
                                              700
ATGCCGTGGTTACTATAACGCCACTAGACCGGCGTCCCAGC

GCCGGATGTGCTGGCTTCAGCGGGCGAGAATCATCGCCGAAGGG
                                              800
CGGCGCTACACGACCGAAGTCGCCGCTCTTAGTAGCGGGCTTCCC
                                              806
```

FIG. 5D

| FIG. 5A | FIG. 5B |
|---------|---------|
| FIG. 5C | FIG. 5D |

FIG. 5

SEQUENCE LISTING

<160> NUMBER OF SEQ ID NOS: 51

<210> SEQ ID NO 1
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (0)...(0)
<223> OTHER INFORMATION: y = t or c

<400> SEQUENCE: 1
cygcttcctg ggttgtgg                                                 18

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (0)...(0)
<223> OTHER INFORMATION: r = g or a

<400> SEQUENCE: 2
ttgrggctgg gtgaagtaag                                               20

<210> SEQ ID NO 3
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (0)...(0)
<223> OTHER INFORMATION: m = a or c
<220> FEATURE:
<221> NAME/KEY: misc_feature
<222> LOCATION: (0)...(0)
<223> OTHER INFORMATION: s = g or c
<220> FEATURE:
<221> NAME/KEY: misc_feature
<222> LOCATION: (0)...(0)
<223> OTHER INFORMATION: w = a or t

<400> SEQUENCE: 3
ggtmtgccga aatswtgg                                                 18

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (0)...(0)

```
<223> OTHER INFORMATION: h = a, c or t

<400> SEQUENCE: 4
cgcagccaga ahatcccgac                                                         20

<210> SEQ ID NO 5
<211> LENGTH: 37
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (0)...(0)
<223> OTHER INFORMATION: y = t or c

<400> SEQUENCE: 5
ccagcgtatg gyaccaccaa cgatatcgcg gcgctgg                                      37

<210> SEQ ID NO 6
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (0)...(0)
<223> OTHER INFORMATION: s = g or c

<400> SEQUENCE: 6
tgtrtgcsca ggcgaacg                                                           18

<210> SEQ ID NO 7
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (0)...(0)
<223> OTHER INFORMATION: y = t or c

<400> SEQUENCE: 7
gtagagcgtc tgtgygttat cg                                                      22

<210> SEQ ID NO 8
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 8
tttatgcgca gacgagtg                                                           18

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
aaagcacctg cgtattatct                                                         20
```

```
<210> SEQ ID NO 10
<211> LENGTH: 32
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (0)...(0)
<223> OTHER INFORMATION: r = g or a

<400> SEQUENCE: 10
cgaggcgcgg cgctggaraa aagcaggcct cg                                32

<210> SEQ ID NO 11
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (0)...(0)
<223> OTHER INFORMATION: y = t or c
<220> FEATURE:
<221> NAME/KEY: misc_feature
<222> LOCATION: (0)...(0)
<223> OTHER INFORMATION: w = a or t

<400> SEQUENCE: 11
gyattcaggc wggactgcc                                                19

<210> SEQ ID NO 12
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 12
gggggataaa accggcag                                                 18

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (0)...(0)
<223> OTHER INFORMATION: r = g or a

<400> SEQUENCE: 13
gctttctgcc ttaggttgrg                                               20

<210> SEQ ID NO 14
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (0)...(0)
<223> OTHER INFORMATION: r = g or a

<400> SEQUENCE: 14
artgaccaga atcagcggc                                                19
```

```
<210> SEQ ID NO 15
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (0)...(0)
<223> OTHER INFORMATION: r = g or a

<400> SEQUENCE: 15
tagcgcgagc attcrggc                                                 18

<210> SEQ ID NO 16
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (0)...(0)
<223> OTHER INFORMATION: k = g or t

<400> SEQUENCE: 16
tgggkagtgg gcgataaa                                                 18

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
tacgattttc gccgccgcag                                               20

<210> SEQ ID NO 18
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (0)...(0)
<223> OTHER INFORMATION: y = t or c

<400> SEQUENCE: 18
gacggytttc cgccttct                                                 18

<210> SEQ ID NO 19
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (0)...(0)
<223> OTHER INFORMATION: y = t or c
<220> FEATURE:
<221> NAME/KEY: misc_feature
<222> LOCATION: (0)...(0)
<223> OTHER INFORMATION: r = g or a
<220> FEATURE:
<221> NAME/KEY: misc_feature
<222> LOCATION: (0)...(0)
<223> OTHER INFORMATION: s = g or c
```

```
-continued

<400> SEQUENCE: 19
ygccgctgtr tgcscaggc                                                 19

<210> SEQ ID NO 20
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (0)...(0)
<223> OTHER INFORMATION: s = g or c

<400> SEQUENCE: 20
acgaygttca rcaaaagc                                                  18

<210> SEQ ID NO 21
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (0)...(0)
<223> OTHER INFORMATION: r = g or a

<400> SEQUENCE: 21
ctcrtcggcg cggtagagc                                                 19

<210> SEQ ID NO 22
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (0)...(0)
<223> OTHER INFORMATION: y = t or c
<220> FEATURE:
<221> NAME/KEY: misc_feature
<222> LOCATION: (0)...(0)
<223> OTHER INFORMATION: r = g or a

<400> SEQUENCE: 22
tatcggcggt gtyaatcarc g                                              21

<210> SEQ ID NO 23
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (0)...(0)
<223> OTHER INFORMATION: r = g or a
<220> FEATURE:
<221> NAME/KEY: misc_feature
<222> LOCATION: (0)...(0)
<223> OTHER INFORMATION: m = a or c

<400> SEQUENCE: 23
crmcgcttta tgcgcagac                                                 19

<210> SEQ ID NO 24
```

```
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (0)...(0)
<223> OTHER INFORMATION: r = g or a
<220> FEATURE:
<221> NAME/KEY: misc_feature
<222> LOCATION: (0)...(0)
<223> OTHER INFORMATION: k = g or t

<400> SEQUENCE: 24
artgcggkgc arcaaaag                                                 18

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (0)...(0)
<223> OTHER INFORMATION: k = g or t
<220> FEATURE:
<221> NAME/KEY: misc_feature
<222> LOCATION: (0)...(0)
<223> OTHER INFORMATION: y = t or c

<400> SEQUENCE: 25
tatctkyggt atcgatgagc                                               20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26
gttcatcacc gcgataaagc                                               20

<210> SEQ ID NO 27
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 27
cagcaccagt aargtgatg                                                19

<210> SEQ ID NO 28
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 28
ttgtagttaa ycargtcyga rg                                            22

<210> SEQ ID NO 29
<211> LENGTH: 18
<212> TYPE: DNA
<213> ORGANISM: Artificial Sequence
```

```
<220> FEATURE:
<223> OTHER INFORMATION: Synthetic oligonucleotide

<400> SEQUENCE: 29
cggtgatgaa cgctttcc                                                  18

<210> SEQ ID NO 30
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 30
atcggcaggc ttgatctc                                                  18

<210> SEQ ID NO 31
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 31
cggcgataag caragtgaaa cgcaaaagat cgccg                               35

<210> SEQ ID NO 32
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 32
ccaccaacga tatcgcg                                                   17

<210> SEQ ID NO 33
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 33
tggyaccacc aacgatatcg cggt                                           24

<210> SEQ ID NO 34
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 34
aactgacact gggctctg                                                  18

<210> SEQ ID NO 35
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 35
atacmctccg caggttcc                                                  18
```

```
<210> SEQ ID NO 36
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 36
cgcgatcaca cgaccggcaa ccaccgcaga tcgcg                               35

<210> SEQ ID NO 37
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 37
gatrgatacc ggctcagg                                                  18

<210> SEQ ID NO 38
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 38
gtaacggatg ggtgtgtc                                                  18

<210> SEQ ID NO 39
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 39
cgcgatcgct gccgctgtgc tggctcggat cgcg                                34

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 40
gacgatgtca ctggctgagc                                                20

<210> SEQ ID NO 41
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 41
agccgccgac gctaataca                                                 19

<210> SEQ ID NO 42
<211> LENGTH: 22
<212> TYPE: DNA
<213> ORGANISM: Artificial Sequence
<220> FEATURE:
<223> OTHER INFORMATION: Synthetic oligonucleotide
```

<400> SEQUENCE: 42
gcgacctggt taactacaat cc                                             22

<210> SEQ ID NO 43
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 43
cggtagtatt gcccttaagc c                                              21

<210> SEQ ID NO 44
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 44
cgctttgcca tgtgcagcac c                                              21

<210> SEQ ID NO 45
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 45
gctcagtacg atcgagcc                                                  18

<210> SEQ ID NO 46
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 46
gctggagaaa agcagcggag                                                20

<210> SEQ ID NO 47
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 47
gtaagctgac gcaacgtctg                                                20

<210> SEQ ID NO 48
<211> LENGTH: 806
<212> TYPE: DNA
<213> ORGANISM: Artificial Sequence
<220> FEATURE:
<223> OTHER INFORMATION: Consensus DNA sequence
<220> FEATURE:
<221> NAME/KEY: misc_feature
<222> LOCATION: (0)...(0)
<223> OTHER INFORMATION: n = a, t, c or g

<400> SEQUENCE: 48

```
tgccgctgta tgcgcaaacg gcggacgtac agcaaaaact tgccgaatta gagcggcagt    60
cgggaggcag actgggtgtg gcattgatta acacagcaga taattcgcaa atactttatc   120
gtgctgatga gcgctttgcg atgtgcagca ccagtaaagt gatggccgcg gccgcggtgc   180
tgaagaaaag tgaaagcgaa ccgaatctgt taaatcagcg agttgagatc aaaaaatctg   240
acctggttaa ctataatncc gattgcggaa aagcacgtca atgggacgat gtcactggct   300
gagcttagcg cggccgcgct acagtacagc gataacgtgg cgatgaataa gctgattgct   360
cacgttggcg gcccggctag cgtcaccgcg ttcgcccgac agctgggaga cgaaacgttc   420
cgtgtcgacc gtaccgagcc gacgttaaac accgccattc cgggcgatcc gcgtgatacc   480
acttcacctc gggcaatggc gcaaactctg cggaatctga cgctgggtaa agcattgggc   540
gacagccaac gggcgcagct ggtgacatgg atgaaaggca ataccaccgg tgcagcgagc   600
attcaggctg gactgcctgc ttcctgggtt gtggggdata aaaccggcag cggtgactat   660
ggcaccacca acgatatcgc ggtgatctgg ccaaaagatc gtgcgccgct gattctggtc   720
acttacttca cccagcctca acctaaggca gaaagccgtc gcgatgtatt agcgtcggcg   780
gctaaaatcg tcaccacggt ttgtaa                                        806
```

<210> SEQ ID NO 49
<211> LENGTH: 806
<212> TYPE: DNA
<213> ORGANISM: Artificial Sequence
<220> FEATURE:
<223> OTHER INFORMATION: Consensus DNA sequence

<400> SEQUENCE: 49

```
caacgctgca tgcgcaggcg aacagcgtgc aacagcagct ggaagccctg gagaaaagtt    60
cgggaggtcg gcttggcgtt gcgctgatta acaccgccga taattcgcag attctctacc   120
gtgccgatga acgttttgcg atgtgcagta ccagtaaggt gatggcggcc gcggcggtgc   180
ttaaacagag cgagagcgat aagcacctgc taaatcagcg cgttgaaatc aagaagagcg   240
acctggttaa ctacaatccc attgcggaga aacacgttaa cggcacgatg acgctggctg   300
agcttggcgc agcggcgctg cagtatagcg acaatactgc catgaataag ctgattgccc   360
atctgggtgg tcccgataaa gtgacggcgt ttgctcgctc gttgggtgat gagaccttcc   420
gtctggacag aaccgagccc acgctcaata ccgccattcc aggcgacccg cgtgataccc   480
ccacgccgct cgcgatggcg cagaccctga aaaatctgac gctgggtaaa gcgctggcgg   540
aaactcagcg ggcacagttg gtgacgtggc ttaagggcaa tactaccggt agcgcgagca   600
ttcgggcggg tctgccgaaa tcatgggtag tgggcgataa aaccggcagc ggagattatg   660
gcaccaccaa cgatatcgcg gttatctggc cggaaaacca cgcaccgctg gttctggtga   720
cctactttac ccaaccggag cagaaggcgg aaagccgtcg ggatattctg gctgcggcgg   780
cgaaaatcgt aacccacggt ttctga                                        806
```

<210> SEQ ID NO 50
<211> LENGTH: 806
<212> TYPE: DNA
<213> ORGANISM: Artificial Sequence
<220> FEATURE:
<223> OTHER INFORMATION: Consensus DNA sequence

<400> SEQUENCE: 50

```
tgccgctgtg tgcccaggcg aacgatgttc aacaaaagct cgcggcgctg gagaaaagca    60 gcggggacg actgggtgtg gcgttgatta acaccgccga taacacgcag acgctctacc   120
```

-continued

```
gcgccgacga gcgttttggc catgtgcagc accagtaaag tgatggcggc agcggcggtg      180
ttaagcaaag tgaaacgcaa aagggcttgt tgagtcagcg ggttgaaatt aagccctcag      240
acttgattaa ctacaacccc attgcggaaa aacacgtcaa tggcacgatg acattcgggg      300
agttgagcgc ggcggcgcta cagtacagcg ataatactgc catgaataag ctgattgccc      360
atctcggggg gccggataaa gtgacggcat ttgcccgtac gattggcgat gacacgttcc      420
ggctcgatcg taccgagccg acgctcaaca ccgcgatccc cggcgacccg cgcgatacca      480
ccacgccgtt agcgatggcg caggctctgc gcaatctgac gttgggcaat gccctgggtg      540
acactcagcg tgcgcagctg gtgatgtggc tgaaaggcaa caccaccggc gctgccagca      600
ttcaggcagg gctacccaca tcgtgggttg tcggggataa aaccggcagc ggcgattatg      660
gtacgacgaa tgatatcgcg gttatttggc cggaaggtcg cgcgccgctc gttctggtga      720
cttacttcac ccagtcggag ccgaaggcag agagccgtcg tgacgtgctc gctgctgccg      780
ccagaattgt caccgacggt tattaa                                           806

<210> SEQ ID NO 51
<211> LENGTH: 806
<212> TYPE: DNA
<213> ORGANISM: Artificial Sequence
<220> FEATURE:
<223> OTHER INFORMATION: Consensus DNA sequence

<400> SEQUENCE: 51
cgccgcttta tgcgcagacg agtgcggtgc agcaaaagct ggcggcgctg gagaaaagca       60
gcggagggcg gctgggcgtc gcgctcatcg ataccgcaga taatacgcag gtgctttatc      120
gcggtgatga acgctttcca atgtgcagta ccagtaaagt tatggcggcc gcggcggtgc      180
ttaagcagag tgaaacgcaa aagcagctgc ttaatcagcc tgtcgagatc aagcctgccg      240
atctggttaa ctacaatccg attgccgaaa aacacgtcaa cggcacaatg acgctggcag      300
aactgagcgc ggccgcgttg cagtacagcg acaataccgc catgaacaaa ttgattgccc      360
agctcggtgg cccgggaggc gtgacggctt ttgcccgcgc gatcggcgat gagacgtttc      420
gtctggatcg cactgaacct acgctgaata ccgccattcc cggcgacccg agagacacca      480
ccacgccgcg ggcgatggcg cagacgttgc gtcagcttac gctgggtcat gcgctgggcg      540
aaacccagcg ggcgcagttg gtgacgtggc tcaaaggcaa tacgaccggc gcagccagca      600
ttcgggccgg cttaccgacg tcgtggactg tgggtgataa gaccggcagc ggcgactacg      660
gcaccaccaa tgatattgcg gtgatctggc cgcagggtcg tgccccgctg gttctggtga      720 cctatttttac ccagccgcaa cagaacgcag agagccgccg cgatgtgctg gcttcagcgg      780
cgagaatcat cgccgaaggg ctgtaa                                           806
```

METHODS FOR THE DETECTION AND IDENTIFICATION OF EXTENDED SPECTRUM BETA LACTAMASES

RELATED APPLICATIONS

The present application is a continuation of, and claims priority to, PCT/US2010/024832, filed Feb. 19, 2010, which designated the United States and was published in English, which claims priority under 35 U.S.C. §119(e) to U.S. Provisional Application Ser. No. 61/153,954, filed on Feb. 19, 2009, by Lippe et al., and entitled "METHODS FOR THE DETECTION AND IDENTIFICATION OF EXTENDED SPECTRUM BETA LACTAMASES," the entire disclosures of which are each herein incorporated by reference in their entireties.

REFERENCE TO SEQUENCE LISTING

The present application is being filed along with a sequence listing in electronic format. The sequence listing is provided as a file entitled GENOM.097C1.txt, created Aug. 17, 2011 which is 19 KB in size. The information in the electronic format of the sequence listing is incorporated herein by reference in its entirety.

BACKGROUND OF THE INVENTION

Field of the Invention

The embodiments disclosed herein relate to molecular diagnostics, and, in particular, diagnostics used to detect and identify microbes carrying extended spectrum beta lactamases (ESBLs), and in particular CTX-M genes.

Description of the Related Art

βlactamases confer resistance against β-lactam drugs. These enzymes destroy the β-lactam ring of the β-lactam antibiotics, such as penicillin, cephalosporins, cephamycins, and carbapenems (ertapenem). These antibiotics have a common element in their molecular structure: a four-atom ring known as a beta-lactam. The lactamase enzyme breaks that ring open, deactivating the molecule's antibacterial properties.

Extended spectrum β-lactamases (ESBLs) are increasingly responsible for nosocomial infections arising around the globe, and alarmingly, for community emergence as well. (Rossolini et al. 2008, CMI). ESBLs are beta-lactamases that hydrolyze extended-spectrum cephalosporins with an oxyimino side chain. These cephalosporins include cefotaxime, ceftriaxone, and ceftazidime, as well as the oxyimino-monobactam aztreonam. Thus ESBLs confer resistance to these antibiotics and related oxyimino-beta lactams. The most well-known ESBLs are derived from the TEM-1, TEM-2, or SHV-1 genes, and include mutations that alter the amino acid configuration around the active site of these β-lactamases. This extends the spectrum of β-lactam antibiotics susceptible to hydrolysis by these enzymes.

TEM and SHV Classical variants, such as TEM and SHV, are actually spreading rapidly across the United States of America after having affected most of Europe, while a new type of ESBLs, CTX-M, is prevalent in South America, Mediterranean and Eastern European countries (Govinden et al. 2007, AJB). The latest, which owns its name to its high activity against cefotaxime, was observed in the late 1980s in Japan, Europe and Argentina, most specifically in Germany in 1989 (Naas et al. 2008, CMI). It is considered to be the most successful group of all (Rasmussen & Hoiby 2004, CJM). Its appearance could be a consequence of the increased use of ceftriaxone and/or cefotaxime to treat bacterial infections, and its origin is known to be from chromosomal genes resident in members of the genus *Kluy-vera*. To this day, over 85 CTX-M derivatives, classified in 5 phylogenetic groups (CTX-M-1, 2, 8, 9 and 25), have been documented according to the Lahey Clinic website, accessible at the world-wide web address lahey.org/Studies.

CTX-M resistance genes are found in *Enterobacteriaceae* and can be transmitted through plasmids between species easily. Enterobacterial species including *Klebsiella pneumoniae*, *Escherichia coli*, and the like possessing the CTX-M genes are considered to be the main cause for urinary tract infection. Other *Enterobacteriaceae*, such as *Enterobacter cloacae*, *Proteus mirabilis*, *Salmonella enterica*, *Enterobacter aerogenes*, as well as *Klebsiella oxytoca*, can also harbor CTX-M genes. Detection of CTX-M resistant strains is especially crucial, as it requires isolation from other patients in hospitals, and would leave only carbapenems as the main treatment for infections.

Until recently, the only way to know a strain's resistance was to perform a manual antimicrobial susceptibility testing. Susceptibility tests suffer from many drawbacks, including the amount of time to obtain a result, i.e., between 48 to 96 hours. First, the operator needs to isolate the bacterial strain from the specimen, which could take up to 48 hours; then proceed with the biochemical identification, which is another 18 to 24 hours, and then with the manual antimicrobial susceptibility testing, which could also take up to 24 hours. In addition to the delay in obtaining results, manual testing methods also suffer from other problems, such as lack of reproducibility due to improper storage of antibiotic disks, improper diffusion of some antibiotic disks, and a lack into the standardization of the process.

The specificity and accuracy of ESBLs detection is critical, as false negative results can lead medical practitioners to design an inappropriate antibiotic regimen, e.g., treatment of an individual with an ESBL infection with third-generation cephalosporins or with aztreonam. This is poses unnecessary risks to the treated individual, and also increases the odds of cross-contamination within a clinical setting, e.g., a hospital. As some strains producing ESBLs will not show in vitro resistance to all third- or fourth-generation cephalosporins using the suggested breakpoints, the Clinical and Laboratory Standard Institute, (CLSI), recommends reporting ESBL-producing Enterobacteriaceae as resistant to penicillins, cephalosporins and aztreonam, because they might end up being clinically resistant (CLSI, M100-S18). The ability of organisms that harbor CTX-M resistance genes to hydrolyze the newer cephalosporins and aztreonam renders their detection even more difficult. CLSI guidelines pose the threat of misdiagnosing the presence of CTX-M-producing strains, depending on the drugs used in both the initial screening and confirmation tests.

The embodiments disclosed herein provide advantages over other methods used to detect and identify bacteria that have ESBLs, e.g., CTX-M resistance genes, including improved specificity, availability of results in a shorter time period, and eliminates the need to perform additional steps, such as agarose gel electrophoresis, to detect ESBLs. (Lartigue et al. 2004, FEMS ML; Pitout et al. 2004, JCM; Pitout et al. 2007, CMI). Furthermore, the embodiments disclosed herein offer advantages over other reported methods for the detection of ESBLs, including CTX-M, in that methods and compositions disclosed herein are specifically designed for the detection and identification newly discovered isoforms of the CTX-M gene, which were not known as of the time of the development of assays described, for example in U.S. Patent Application Publication No. US20070248954. The methods disclosed in US20070248954 use primers that are not fully complementary to the sequences of the newly

SUMMARY OF THE INVENTION

Compositions and methods for the rapid and sensitive detection of ESBLs, including CTX-M genes that confer antibiotic resistance are provided. The compositions include oligonucleotide primer and probe sets for use in detecting the presence CTX-M nucleic acids, and/or other ESBL nucleic acids, in a sample. These primers and probe sets can be used in amplification methods (such as PCR, particularly quantitative PCR) and packaged into kits for use in amplification methods for the purpose of detecting the presence of a ESBL gene in a test sample, particularly a patient sample, whereby detection of the gene is indicative that the sample comprises a bacterium that has an ESBL.

Thus, in one embodiment, the present invention provides for oligonucleotide primers and probes that comprise, consist essentially of, or consist of at least 10 consecutive nucleotides of the sequences set forth in SEQ ID NOs: 1-24. Primers and/or probes disclosed herein can be used in a method of detecting and or identifying the presence of microbe with extended spectrum beta-lactamases, e.g., CTX-M, in a specimen.

Further provided are kits useful for the detection of an ESBL gene, e.g., CTX-M, in a sample, where the kits comprise a composition according to the embodiments disclosed herein. In some embodiments, the kits can include instructions for using the provided composition in a polymerase-based amplification reaction, for example, PCR or QPCR.

Other embodiments relate to a method of detecting: obtaining a sample from the specimen to be analyzed for the presence of extended spectrum β-lactamases, e.g., CTX-M, and contacting the sample with a set of amplification primers under standard PCR conditions, wherein the set of amplification primers comprises at least one primer pair, wherein said set of primers comprises one or more primers with a universal base, wherein said primer pair hybridizes to nucleic acids flanking a target sequence within an extended spectrum β-lactamase gene, e.g., CTX-M, and wherein said primer pair generates a target amplification product; providing reagents and conditions for extension of the primers to generate the target amplification product; and determining the presence and/or amount of the target amplification product.

The present invention also relates to use of the primers and probes according to the embodiments disclosed herein, wherein the primers or probes have the sequences according to any of the sequences as defined in SEQ ID NOS: 1-24.

DETAILED DESCRIPTION OF THE PREFERRED EMBODIMENT

Figure 1B:
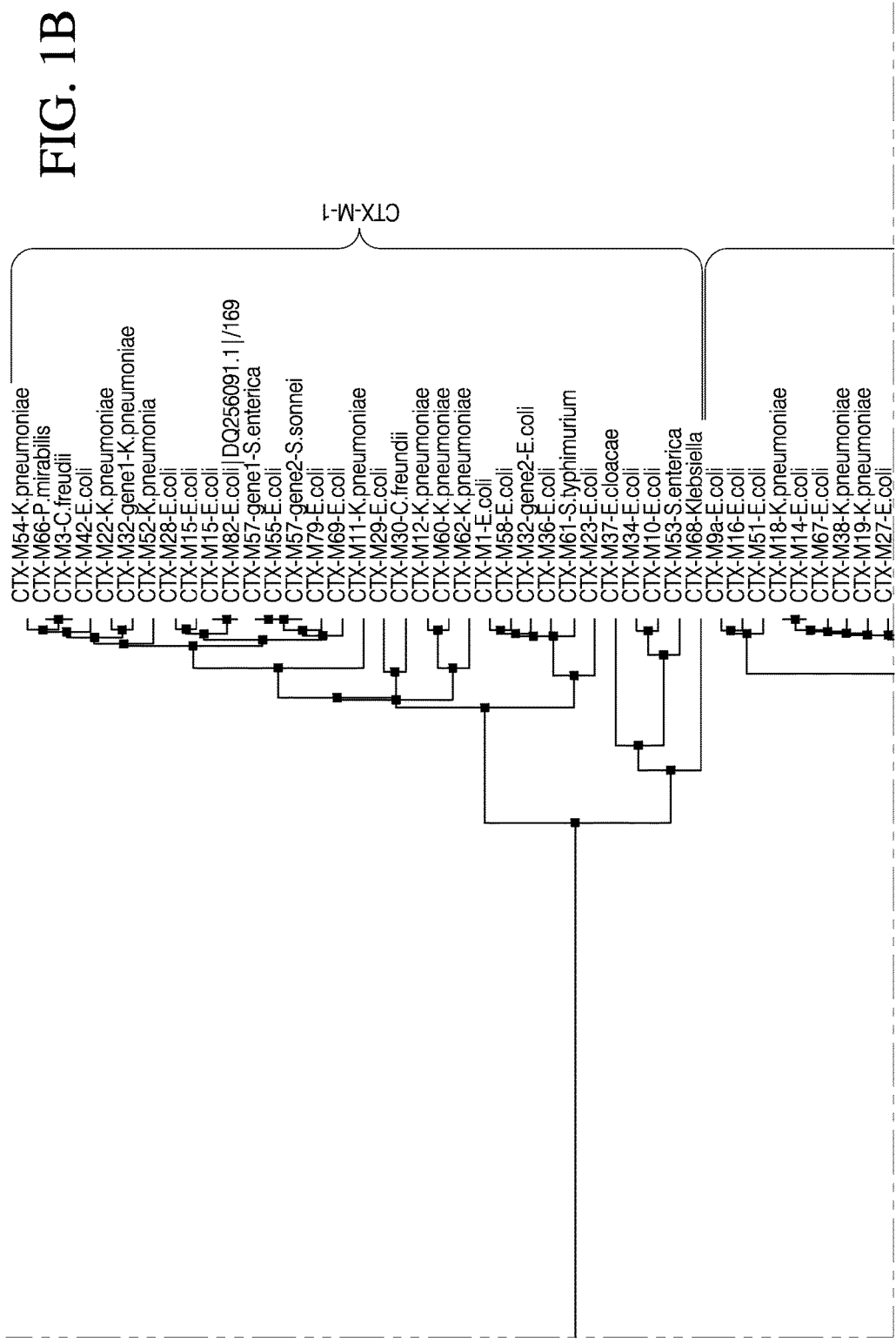
FIG. 1 is a phylogenetic tree of all CTX-M genes clustered in 4 groups, with *Klebsiella oxytoca* as an outgroup.
Figure 1C:
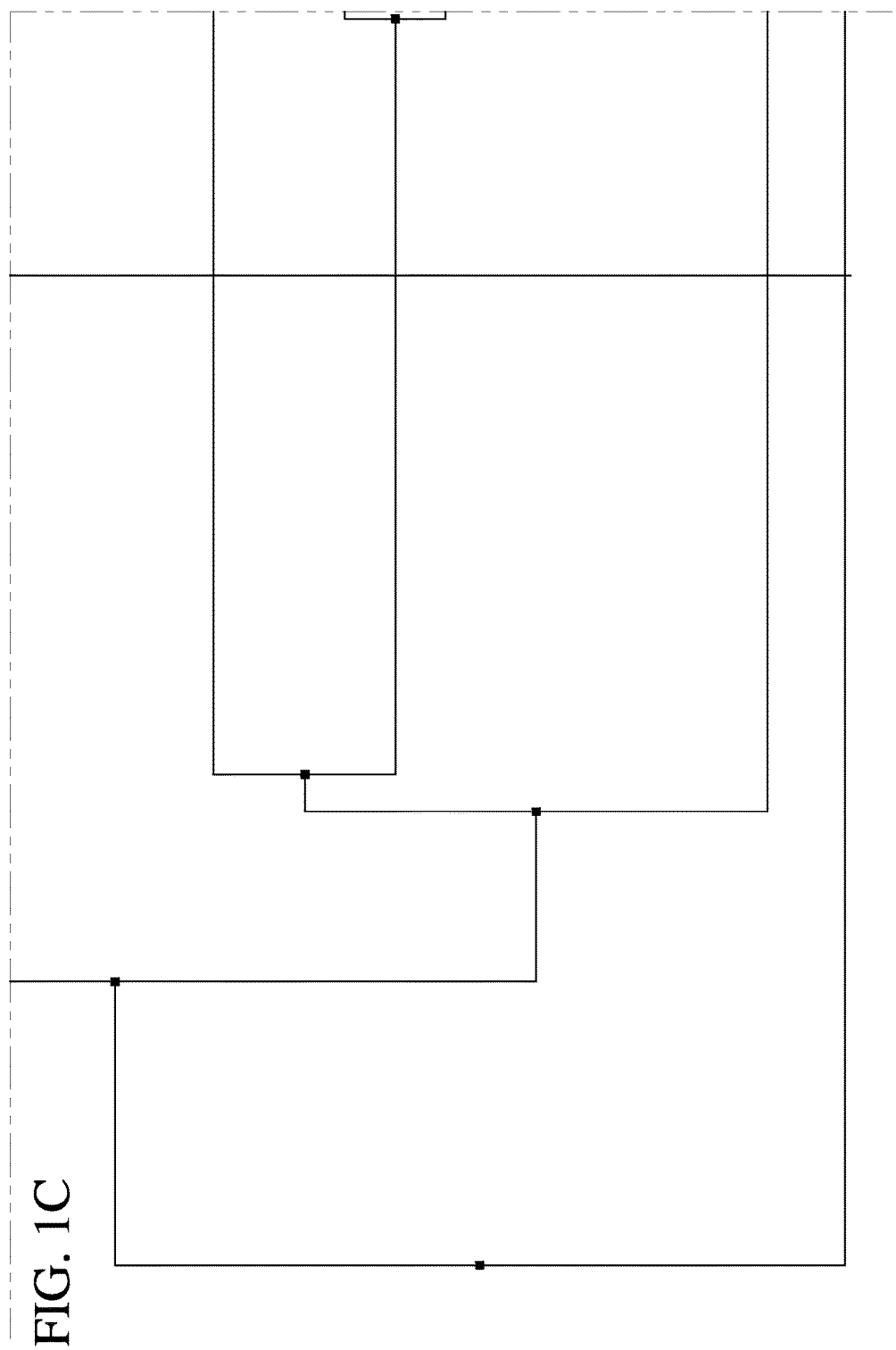
Figure 1D:
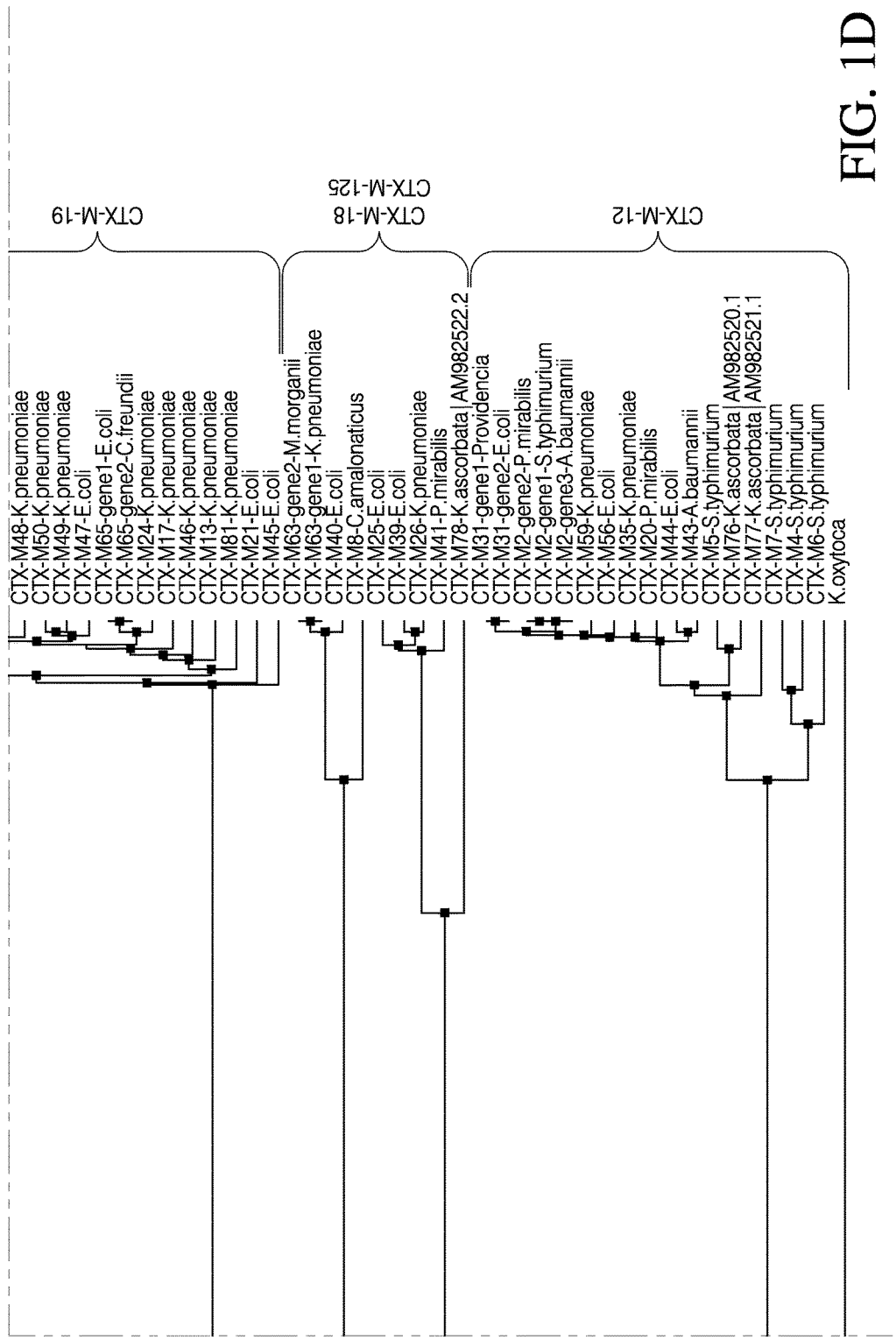
Figure 2A:
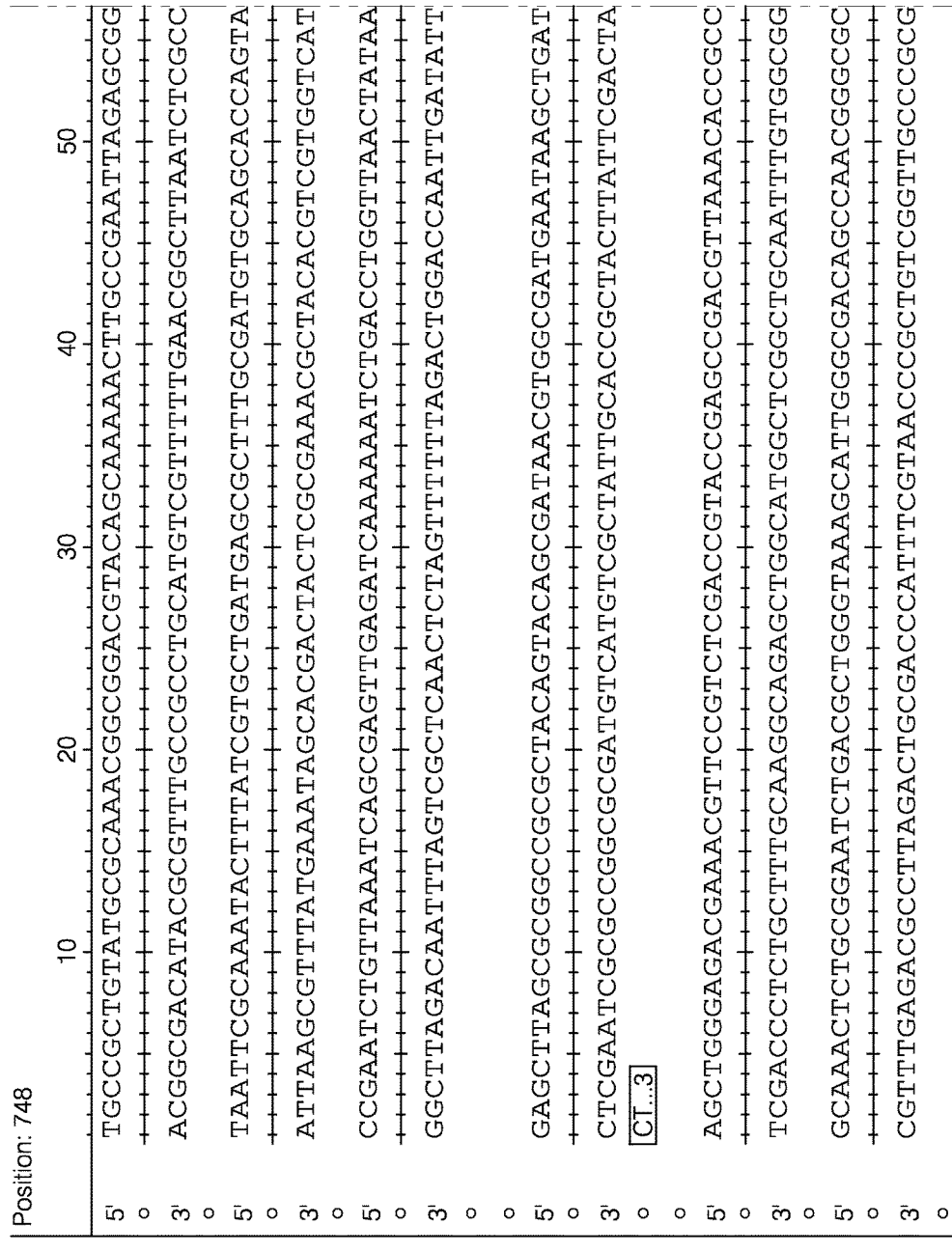
FIG. 2 is a sequence alignment, showing the location of primers disclosed herein to detect the CTX-M-1 group (ctxm1-616F/SEQ ID NO:1)(ctxm1-740R/SEQ ID NO:2)(ctxm1/2-657B/SEQ ID NO:5). Also shown are amplification primers previously disclosed (CTXM1-F3/SEQ ID NO:40)(CTXM1-R2/SEQ ID NO:41). The reference sequence shown is a consensus sequence from an alignment of all CTX-M-1 sequences. The consensus sequence shown corresponds to SEQ ID NO: 48.
Figure 2B:
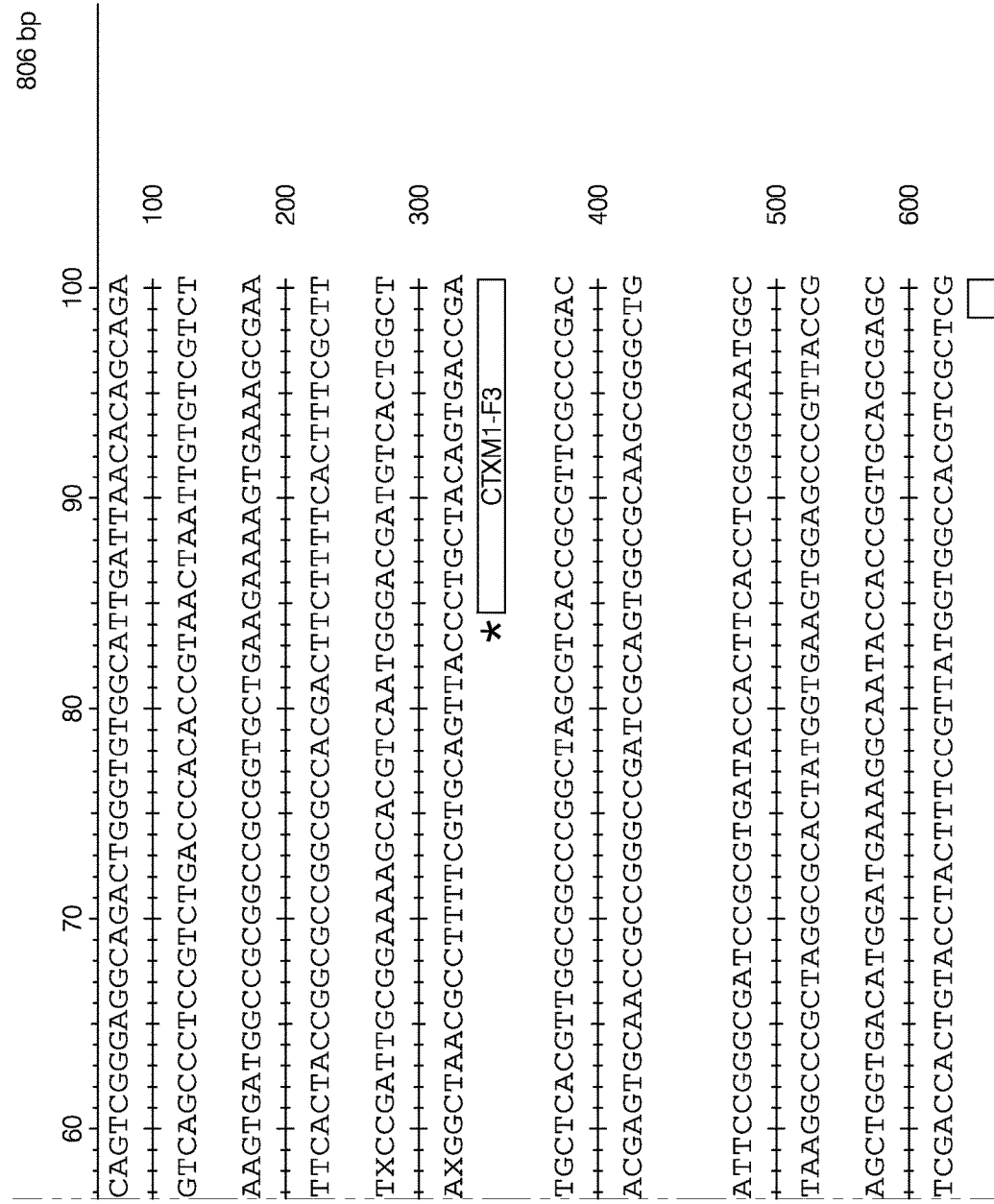
Figure 2C:
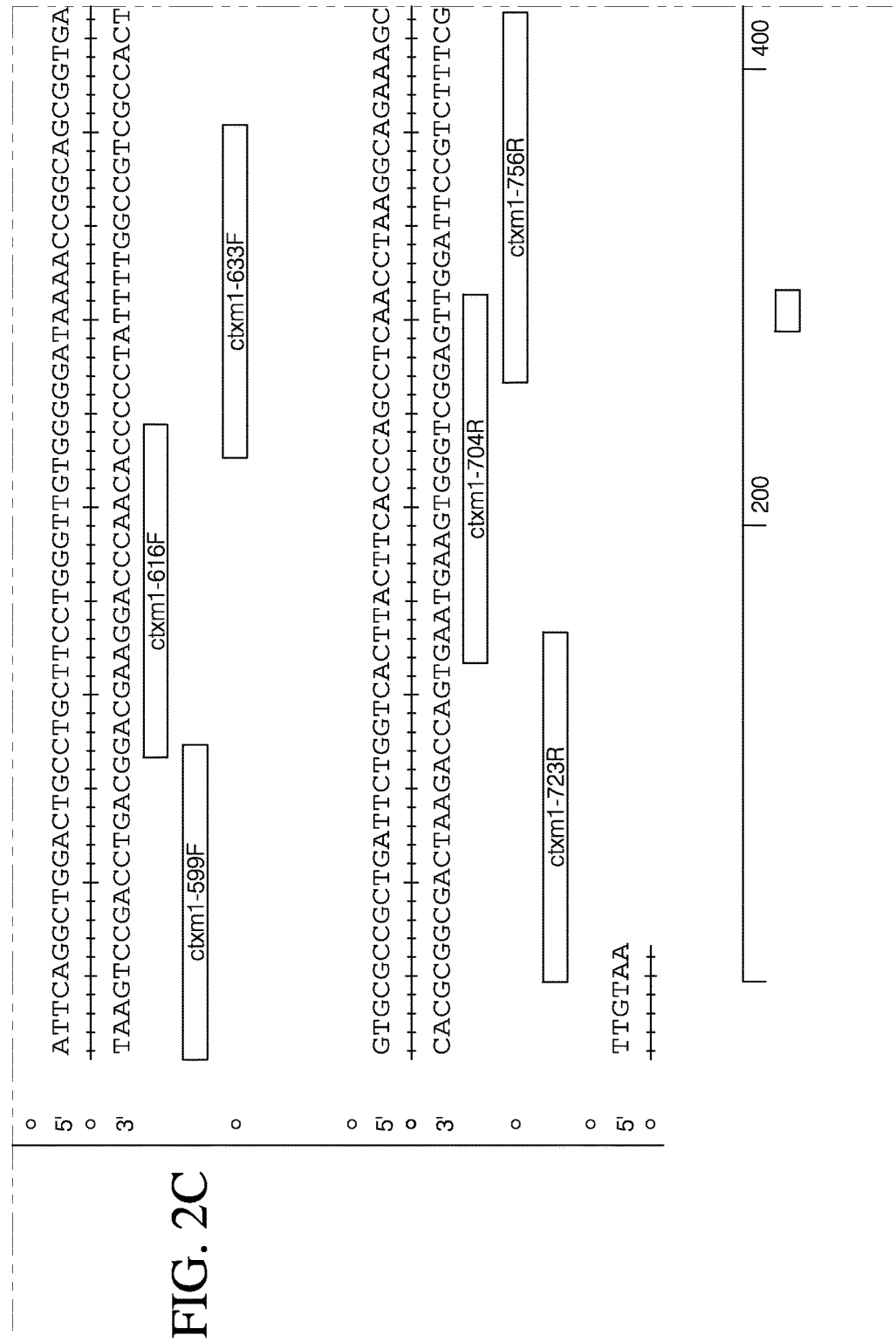
Figure 3A:
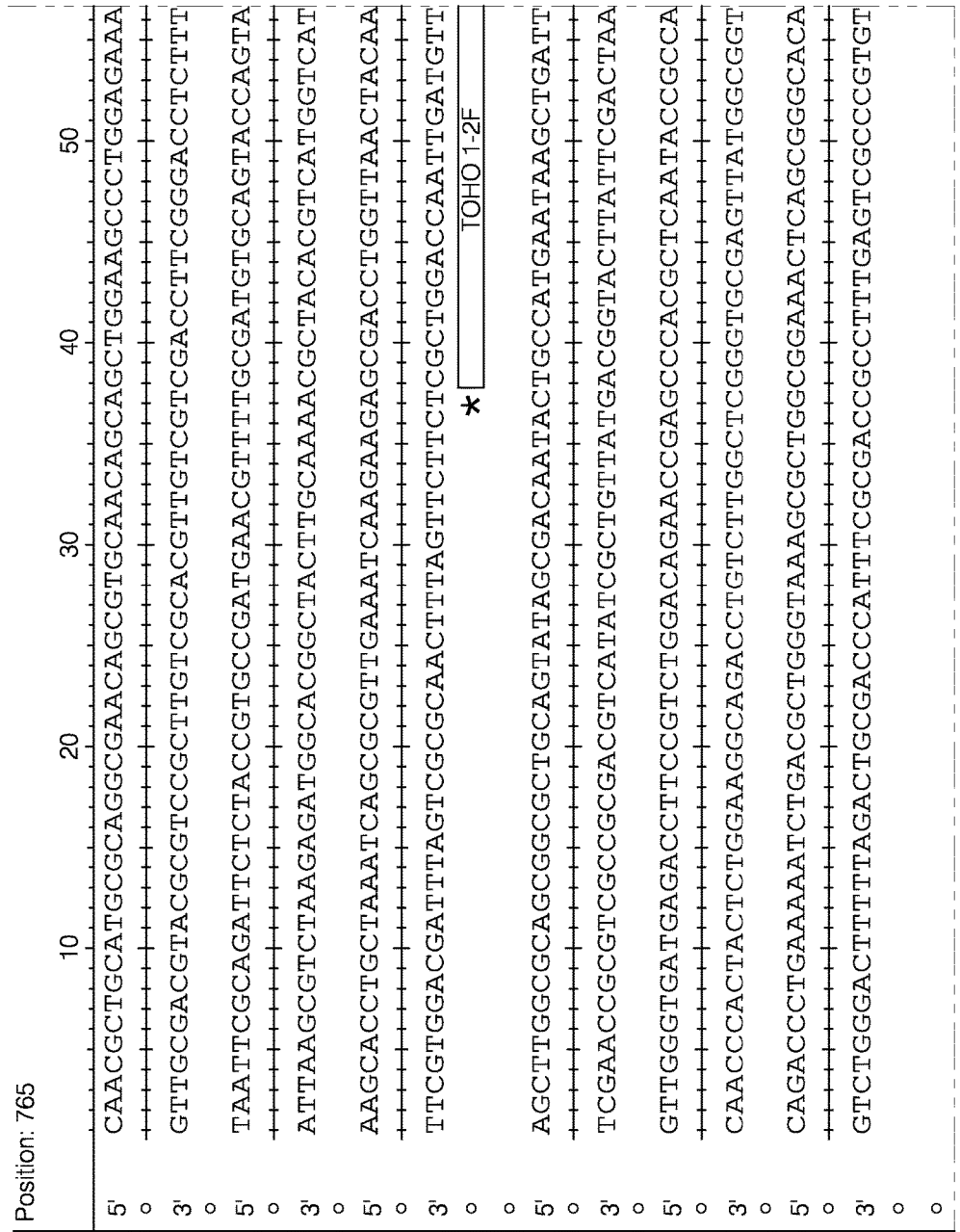
FIG. 3 is a sequence alignment, showing the location of primers disclosed herein to detect the CTX-M-2 group (ctxm2-609F/SEQ ID NO:3)(ctxm2-776R/SEQ ID NO:4) (ctxm1/2-657B/SEQ ID NO:5). Also shown are amplification primers previously disclosed (TOHO1-2F/SEQ ID NO:42)(TOHO 1-1R/SEQ ID NO:43). The reference sequence shown is a consensus sequence from an alignment of all CTX-M-2 sequences. The consensus sequence shown corresponds to SEQ ID NO: 49.
Figure 3B:
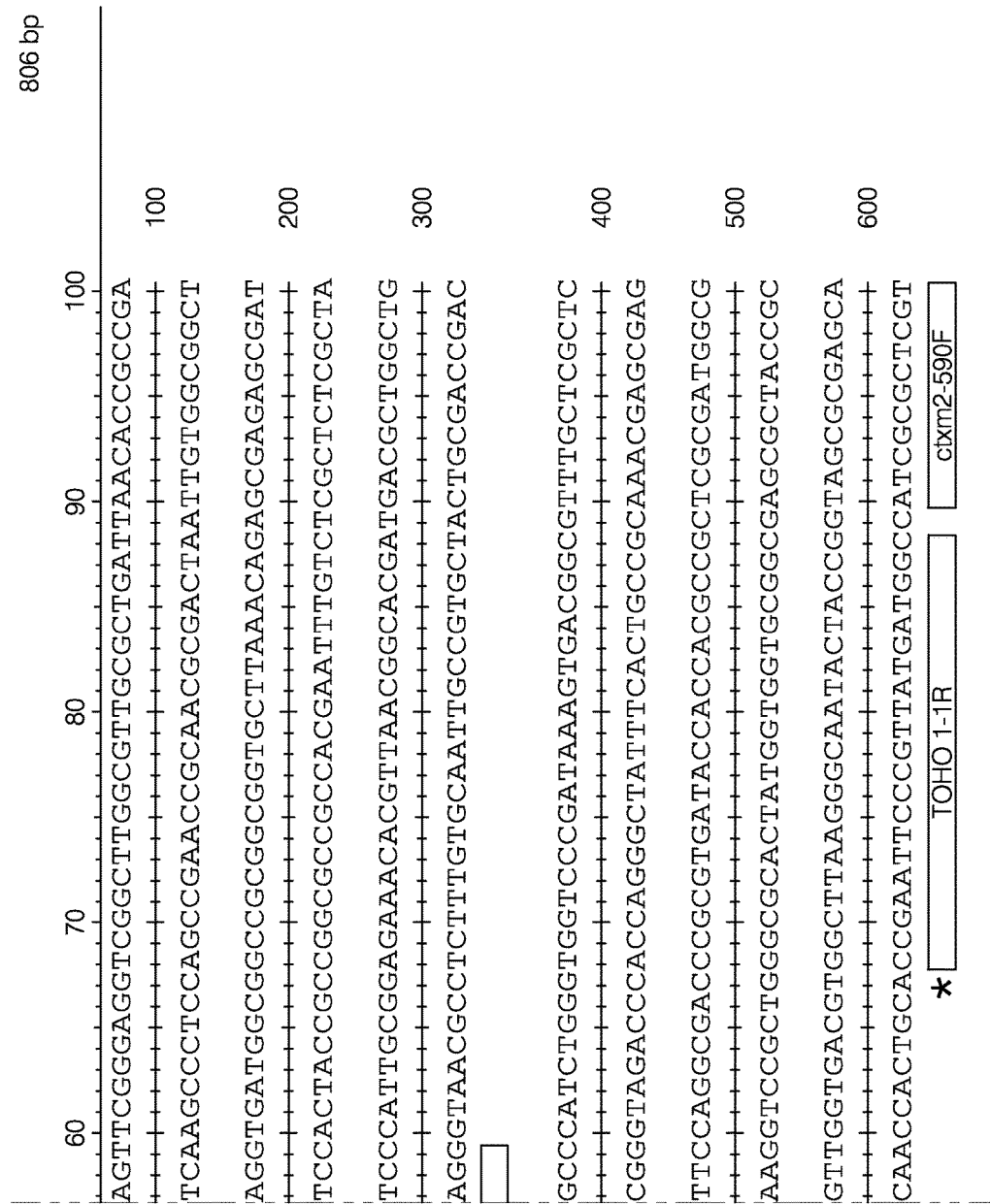
Figure 4A:
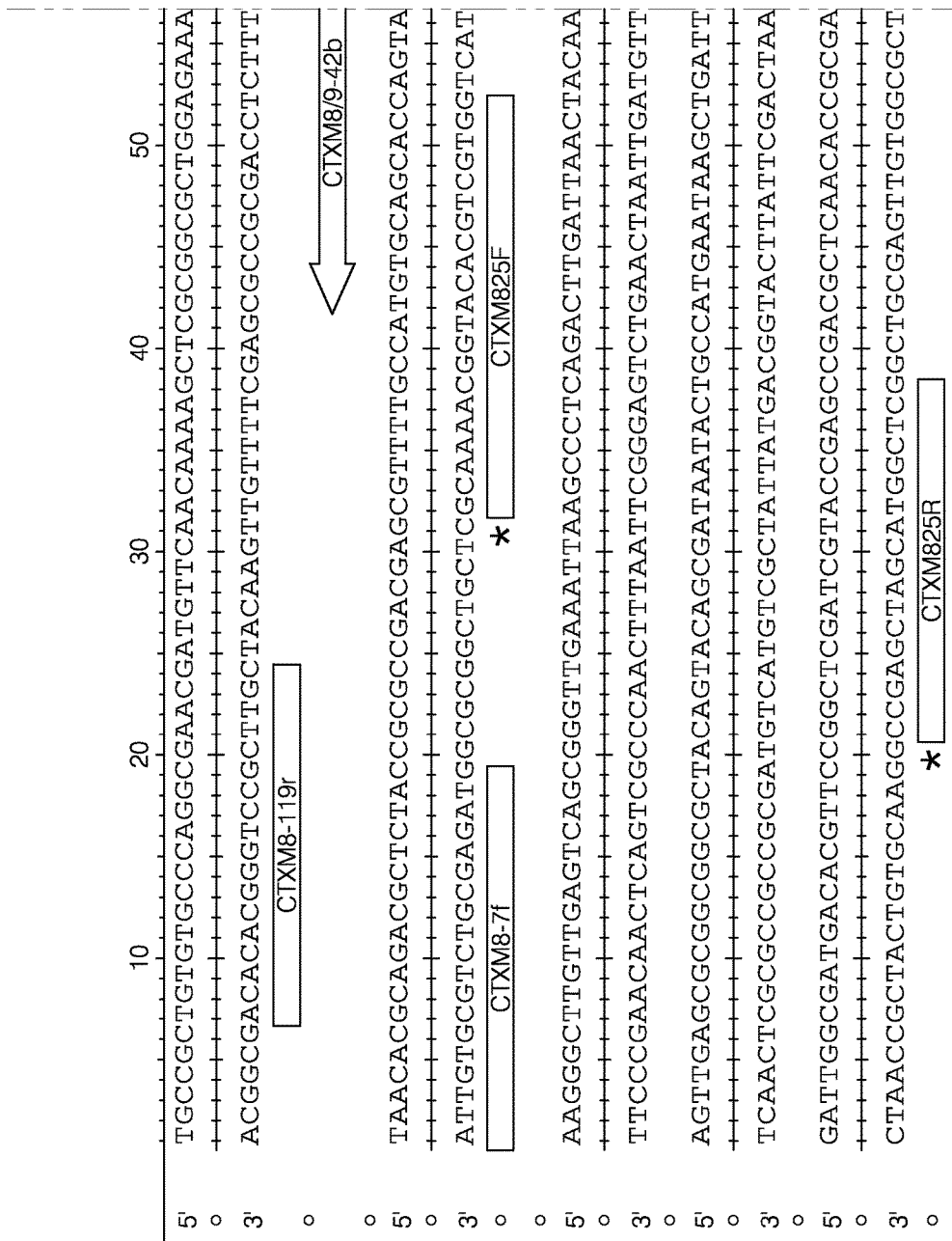
FIG. 4 is a sequence alignment, showing the location of primers disclosed herein to detect the CTX-M-8 group (ctxm8-119R/SEQ ID NO:7)(ctxm8-7F/SEQ ID NO:6) (ctxm8/9-42B/SEQ ID NO:10). Also shown are amplification primers previously disclosed (CTXM825F/SEQ ID NO:44)(CTXM825/SEQ ID NO:45). The reference sequence shown is a consensus sequence from an alignment of all CTX-M-8 sequences. The consensus sequence shown corresponds to SEQ ID NO: 50.
Figure 4B:
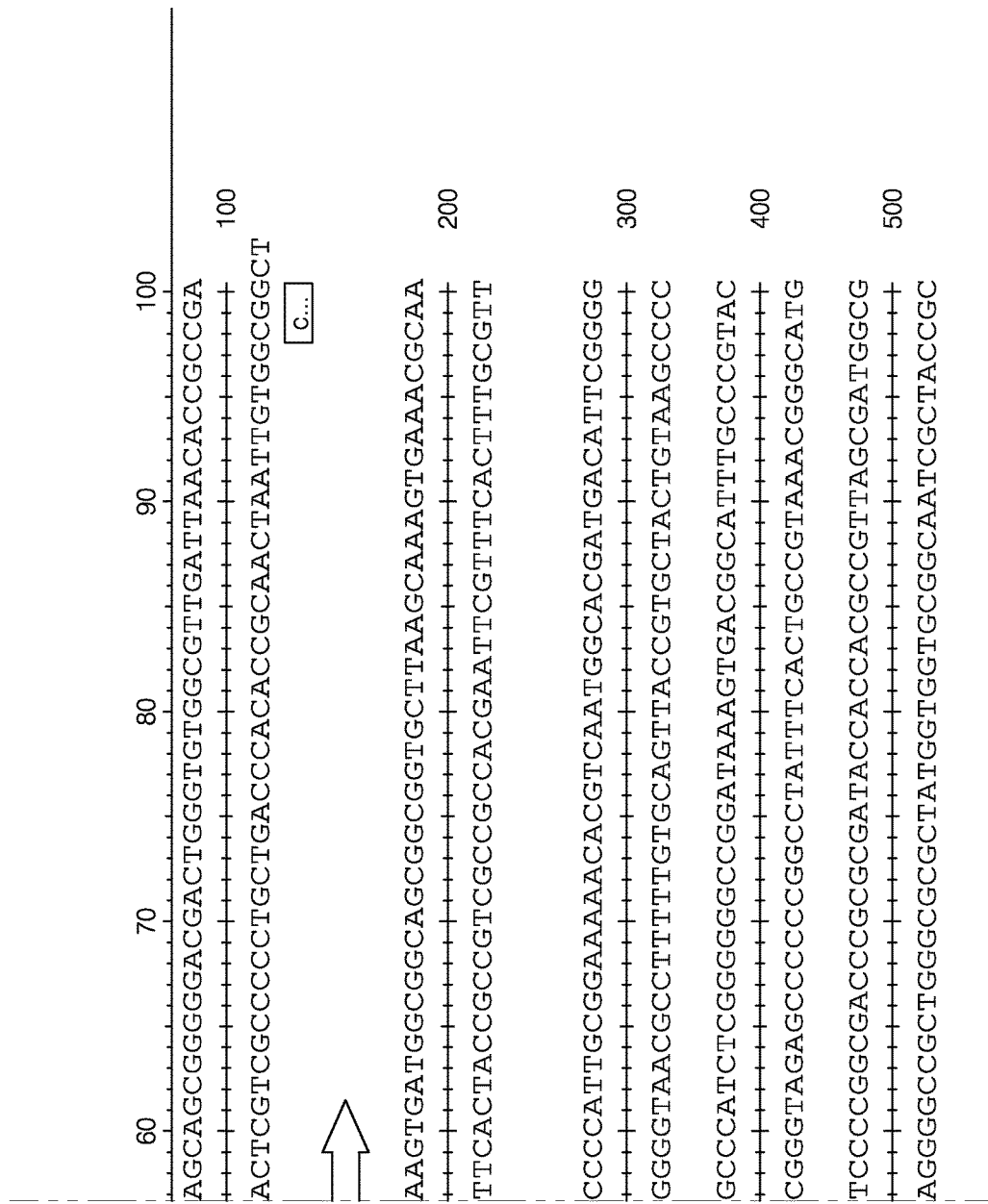
Figure 5A:
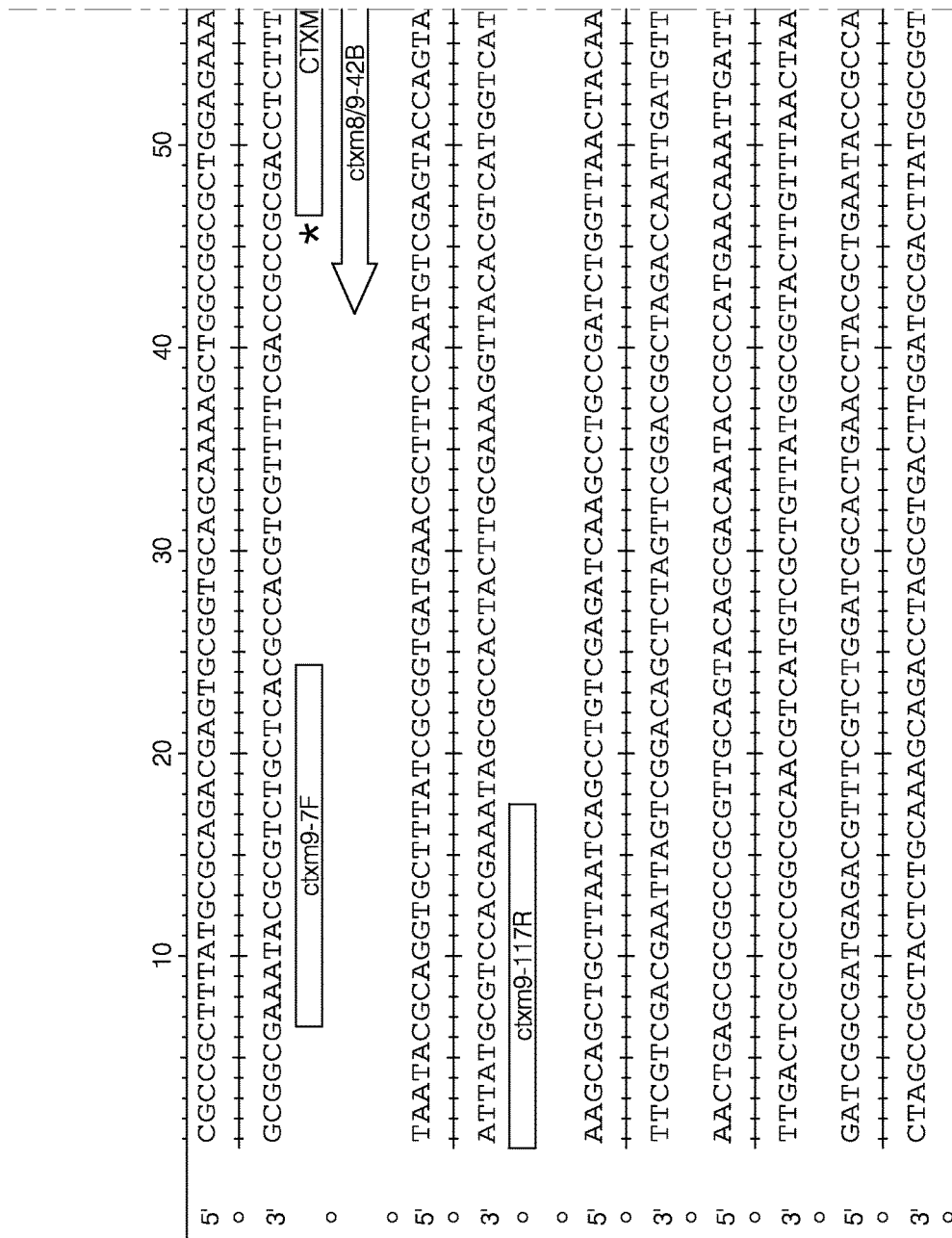
FIG. 5 is a sequence alignment, showing the location of primers disclosed herein to detect the CTX-M-9 group (ctxm9-7F/SEQ ID NO:8)(ctxm9-117R/SEQ ID NO:9) (ctxm8/9-42B/SEQ ID NO:10). Also shown are amplification primers previously disclosed (CTXM914F/SEQ ID NO:46)(CTXM914R/SEQ ID NO:47). The reference sequence shown is a consensus sequence from an alignment of all CTX-M-9 sequences. The consensus sequence shown corresponds to SEQ ID NO: 51.
Figure 5B:
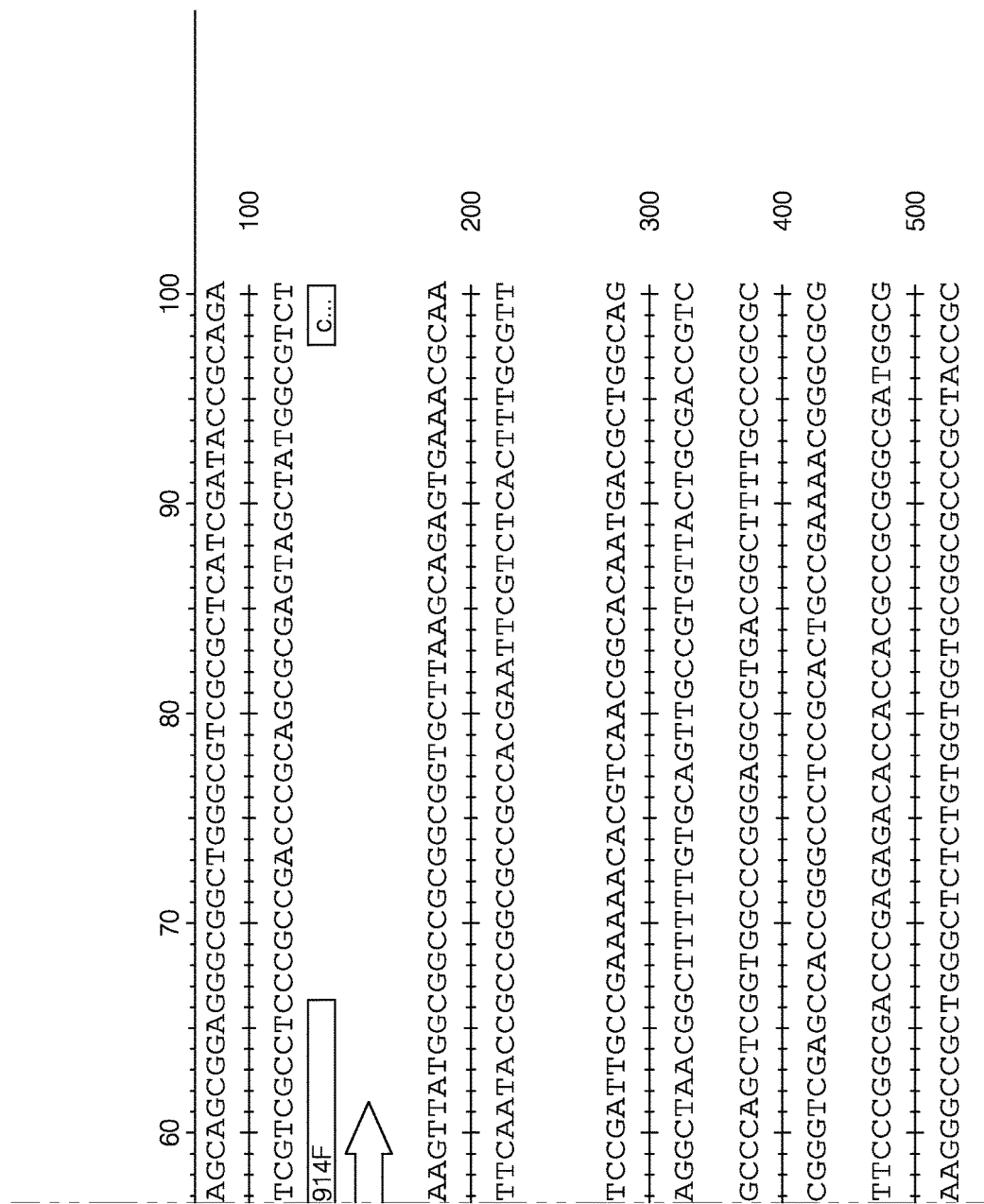

The embodiments disclosed herein relate to compositions and methods for the efficient and specific detection and/or identification of microbes that have extended, or expanded-spectrum β-lactamases (ESBLs).

As used herein, the term "expanded-spectrum β-lactamases" or "ESBLs", refers to β-lactamases that -lactamases capable of conferring bacterial resistance to the penicillins, first-, second-, and third-generation cephalosporins, and aztreonam (but not the cephamycins or carbapenems) by hydrolysis of these antibiotics, and which are inhibited by β-lactamase inhibitors such as clavulanic acid. The skilled artisan will appreciate that the term "ESBL" encompasses all expanded-spectrum β-lactamases now known or discovered in the future, including but not limited to all ESBLs listed on the Lahey Clinic website, at the world-wide web address lahey.org/Studies. Accordingly, the term ESBL encompasses ESBLs of the SHV, or sulfhydryl variable, type, TEM-type, TOHO and CTX-M type.

In some embodiments, the compositions and assays are used to detect and identify CTX-M beta-lactamases. The CTX-M enzymes have been previously reviewed in detail (Bonnet, R., et al. (2004), Growing group of extended-spectrum beta-lactamases: the CTX-M enzymes. Antimicrob. Agents Chemother. 48:1-14.). Some exemplary, non-limiting characteristics of CTX-M beta lactamases are as follows: cefotaxime MICs in the resistant range (>64 µg/ml), while ceftazidime MICs are usually in the apparently susceptible range (2 to 8 µg/ml). However, some CTX-M-type ESBLs can actually hydrolyze ceftazidime and confer resistance to this cephalosporin (MICs as high as 256 µg/ml). Aztreonam MICs are variable. CTX-M-type β-lactamases hydrolyze cefepime, and cefepime MICs are higher than observed in bacteria producing other ESBL types. Tazobactam exhibits an almost 10-fold greater inhibitory activity than clavulanic acid against CTX-M-type β-lactamases. Some bacteria may harbor both CTX-M-type and SHV-type ESBLs or CTX-M-type ESBLs and AmpC-type β-lactamases, which may alter the antibiotic resistance phenotype.

The embodiments disclosed herein are capable of rapid detection and/or identification of CTX-M β-lactamases, including one or more CTX-M β-lactamases identified as CTX-M-1 through CTX-M-82, including some or all of the CTX-M type β-lactamases found in the bacterial strains listed in Table 1.

TABLE 1

| Group | Enzyme | Nucleotide Position on the group alignment | Base Change | Genbank Accession No. | Species |
|---|---|---|---|---|---|
| CTX-M-1 | CTX-M-1 | | | X92506 | *Escherichia coli* |
| | CTX-M-3 | | | Y10278 | *Citrobacter freundii* |
| | CTX-M-10 | R 4 | A → G | AF255298 | *Escherichia coli* |
| | | B 6 | C → T | | |
| | CTX-M-11 | F 2 | T → C | AY005110 | *Klebsiella pneumoniae* |
| | CTX-M-12 | | | AF305837 | *Klebsiella pneumoniae* |
| | CTX-M-15 | | | AY044436 | *Escherichia coli* |
| | CTX-M-22 | | | AY080894 | *Klebsiella pneumoniae* |
| | CTX-M-23 | | | AF488377 | *Escherichia coli* |
| | CTX-M-28 | | | AJ549244 | *Escherichia coli* |
| | CTX-M-29 | | | AY267213 | *Escherichia coli* |
| | CTX-M-30 | | | AY292654 | *Citrobacter freundii* |
| | CTX-M-32 | | | AJ557142 | *Escherichia coli* |
| | | | | AY421962 | *Klebsiella pneumoniae* |
| | CTX-M-34 | R 4 | A → G | AY515297 | *Escherichia coli* |
| | | B 6 | C → T | | |
| | CTX-M-36 | | | AB177384 | *Escherichia coli* |
| | CTX-M-37 | R 4 | A → G | AY649755 | *Enterobacter cloacae* |
| | | B 6 | C → T | | |
| | CTX-M-42 | | | DQ061159 | *Escherichia coli* |
| | CTX-M-52 | | | DQ223685 | *Klebsiella pneumoniae* |
| | CTX-M-53 | R 4 | A → G | DQ268764 | *Salmonella enterica* |
| | | B 6 | C → T | | |
| | CTX-M-54 | | | DQ303459 | *Klebsiella pneumoniae* |
| | CTX-M-55 | | | DQ885477 | *Escherichia coli* |
| | CTX-M-57 | | | DQ810789 | *Salmonella enterica* |
| | | | | EU086736 | *Shigella sonnei* |
| | CTX-M-58 | | | EF210159 | *Escherichia coli* |
| | CTX-M-60 | | | AM411407 | *Klebsiella pneumoniae* |
| | CTX-M-61 | | | EF219142 | *Salmonella typhimurium* |
| | CTX-M-62 | | | EF219134 | *Klebsiella pneumoniae* |
| | CTX-M-66 | | | EF576988 | *Proteus mirabilis* |
| | CTX-M-68 | B 6 | C → T | EU177100 | *Klebsiella* sp. |
| | CTX-M-69 | | | EU402393 | *Escherichia coli* |
| | CTX-M-79 | | | EF426798 | *Escherichia coli* |
| | CTX-M-82 | | | DQ256091 | *Escherichia coli* |
| CTX-M-2 | CTX-M-2 | | | X92507 | *Salmonella typhimurium* |
| | | | | AB176535 | *Acinetobacter baumannii* |
| | | | | AJ416343 | *Proteus mirabilis* |
| | CTX-M-4 | F 4 | C → A | Y14156 | *Salmonella typhimurium* |
| | CTX-M-5 | R 12 | T → C | U95364 | *Salmonella typhimurium* |
| | CTX-M-6 | F 14 | C → G | AJ005044 | *Salmonella typhimurium* |
| | | F 15 | A → T | | |
| | | R 12 | T → C | | |
| | CTX-M-7 | R 12 | T → C | AJ005045 | *Salmonella typhimurium* |
| | CTX-M-20 | R 12 | T → A | AJ416344 | *Proteus mirabilis* |
| | CTX-M-31 | | | AJ567481 | *Providencia* sp. |
| | | | | AJ567482 | *Escherichia coli* |
| | CTX-M-35 | | | AB176532 | *Klebsiella pneumoniae* |
| | CTX-M-43 | | | DQ102702 | *Acinetobacter baumannii* |
| | CTX-M-44 | | | D37830 | *Escherichia coli* |
| | CTX-M-56 | | | EF374097 | *Escherichia coli* |
| | CTX-M-59 | | | DQ408762 | *Klebsiella pneumoniae* |
| | CTX-M-76 | R 12 | T → C | AM982520 | *Kluyvera ascorbata* |
| | CTX-M-77 | R 12 | T → C | AM982521 | *Kluyvera ascorbata* |
| CTX-M-8 | CTX-M-8 | F 4 | G → A | AF189721 | *Citrobacter amalonaticus* |
| | | F 8 | C → G | | |
| | | R 15 | C → T | | |
| | CTX-M-25 | | | AF518567 | *Escherichia coli* |
| | CTX-M-26 | | | AY157676 | *Klebsiella pneumoniae* |
| | CTX-M-39 | | | AY954516 | *Escherichia coli* |
| | CTX-M-40 | F 4 | G → A | AY750914 | *Escherichia coli* |
| | | F 8 | C → G | | |
| | | R 15 | C → T | | |
| | CTX-M-41 | | | DQ023162 | *Proteus mirabilis* |
| | CTX-M-63 | F 4 | G → A | AB205197 | *Klebsiella pneumoniae* |
| | | F 8 | C → G | EU660216 | *Morganella morganii* |
| | | R 15 | C → T | | |
| | CTX-M-78 | F 4 | G → A | AM982522 | *Kluyvera ascorbata* |
| | | F 11 | G → A | | |
| CTX-M-9 | CTX-M-9 | | | AF174129 | *Escherichia coli* |
| | CTX-M-13 | | | AF252623 | *Klebsiella pneumoniae* |
| | CTX-M-14 | | | AF252622 | *Escherichia coli* |
| | CTX-M-16 | | | AY029068 | *Escherichia coli* |
| | CTX-M-17 | | | AY033516 | *Klebsiella pneumoniae* |

TABLE 1-continued

| Group | Enzyme | Nucleotide Position on the group alignment | Base Change | Genbank Accession No. | Species |
|---|---|---|---|---|---|
| | CTX-M-18 | | | AF325133 | *Klebsiella pneumoniae* |
| | CTX-M-19 | | | AF325134 | *Klebsiella pneumoniae* |
| | CTX-M-21 | B 12 | G → A | AJ416346 | *Escherichia coli* |
| | CTX-M-24 | | | AY143430 | *Klebsiella pneumoniae* |
| | CTX-M-27 | | | AY156923 | *Escherichia coli* |
| | CTX-M-38 | | | AY822595 | *Klebsiella pneumoniae* |
| | CTX-M-45 | | | D89862 | *Escherichia coli* |
| | CTX-M-46 | F 16 | G → A | AY847147 | *Klebsiella pneumoniae* |
| | CTX-M-47 | | | AY847143 | *Escherichia coli* |
| | CTX-M-48 | F 16 | G → A | AY847144 | *Klebsiella pneumoniae* |
| | CTX-M-49 | | | AY847145 | *Klebsiella pneumoniae* |
| | CTX-M-50 | | | AY847146 | *Klebsiella pneumoniae* |
| | CTX-M-51 | | | DQ211987 | *Escherichia coli* |
| | CTX-M-65 | | | EF418608 | *Escherichia coli* |
| | | | | EF394372 | *Citrobacter freundii* |
| | CTX-M-67 | | | EF581888 | *Escherichia coli* |
| | CTX-M-81 | | | EU136031 | *Klebsiella pneumoniae* |

Specimens and Samples

The embodiments disclosed herein can be used to detect and/or identify ESBLs in a specimen. As used herein, the term "specimen" can refer to a clinical specimen or sample from one or any number of sources, including, but not limited to, bodily fluids (including, but not limited to, blood, urine, serum, lymph, saliva, anal and vaginal secretions, perspiration, peritoneal fluid, pleural fluid, effusions, ascites, and purulent secretions, lavage fluids, drained fluids, brush cytology specimens, biopsy tissue, explanted medical devices, infected catheters, pus, biofilms and semen) of virtually any organism, with mammalian samples, particularly human samples, and environmental samples (including, but not limited to, air, agricultural, water and soil samples) finding use in the invention. In addition, samples can be taken from food processing, which can include both input samples (e.g. grains, milk or animal carcasses), samples in intermediate steps of processing, as well as finished food ready for the consumer. In some embodiments, the methods and assays described herein can be performed directly on a sample or clinical specimen, without further manipulation of the specimen. In some embodiments, the specimen is manipulated, e.g., cultured, processed to extract nucleic acids, or purified, expanded, or otherwise manipulated.

Primers and Probes

In some embodiments, the specimen or sample can be contacted with a set of amplification primers. In some embodiments, the specimen or sample can be contacted with a probe. As used herein, the terms "primer" and "probe" include, but are not limited to oligonucleotides or nucleic acids. The terms "primer" and "probe" encompass molecules that are analogs of nucleotides, as well as nucleotides. Nucleotides and polynucleotides, as used herein shall be generic to polydeoxyribonucleotides (containing 2-deoxy-D-ribose), to polyribonucleotides (containing D-ribose), to any other type of polynucleotide which is an N- or C-glycoside of a purine or pyrimidine base, and to other polymers containing nonnucleotidic backbones, for example, polyamide (e.g., peptide nucleic acids (PNAs)) and polymorpholino (commercially available from the Anti-Virals, Inc., Corvallis, Oreg., as NEUGENE™ polymers), and other synthetic sequence-specific nucleic acid polymers providing that the polymers contain nucleobases in a configuration which allows for base pairing and base stacking, such as is found in DNA and RNA.

In some embodiments, the "primers" or "probes" disclosed herein can contain locked nucleic acids (LNA). "Locked nucleic acids" (LNAs) are ribonucleotides which contain a methylene bridge which joins the 2' oxygen of the ribose with the 4' carbon (see FIG. 27). Braasch D. A. and Corey, D. R. (2001), Locked nucleic acids (LNA); fine-tuning the recognition of DNA and RNA. Chem. Biol. 8, 1-7, provide an overview of LNAs. This article is herein explicitly incorporated by reference in its entirety. LNAs are available commercially, for example, from the company Proligo, Boulder, Colo., USA. Phosphorothioates are also known to the person skilled in the art and may be ordered, for example, from MWG-Biotech AG, Ebersberg, Germany. Accordingly, in some embodiments, the "primers" or "probes" disclosed herein can include 1, 2, 3, 4, 5, 6, 7, 8, 9, 10, or more LNAs.

The terms nucleotide and polynucleotide include, for example, 3'-deoxy-2',5'-DNA, oligodeoxyribonucleotide N3'→P5' phosphoramidates, 2'-O-alkyl-substituted RNA, double- and single-stranded DNA, as well as double- and single-stranded RNA, DNA:RNA hybrids, and hybrids between PNAs and DNA or RNA. The terms also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides will also include modifications on the sugar moiety, e.g., wherein one or more of the hydroxyl groups are replaced with a halogen, an aliphatic group, or are functionalized as ethers, amines, or the like. Other modifications to nucleotides or polynucleotides involve rearranging, appending, substituting for, or otherwise altering functional groups on the purine or pyrimidine base which form hydrogen bonds to a respective complementary pyrimidine or purine. The resultant modified nucleotide or polynucleotide may form a base pair with other such modified nucleotidic units but not with A, T, C, G or U. For example, guanosine (2-amino-6-oxy-9-beta.-D-ribofuranosyl-purine) may be modified to form isoguanosine (2-oxy-6-amino-9-.beta.-D-ribofuranosyl-purine). Such modification results in a nucleoside base which will no longer effectively form a standard base pair with cytosine. However, modification of cytosine (1-.beta.-D-ribofuranosyl-2-oxy-4-amino-pyrimidine) to form isocytosine (1-β-D-ribofuranosyl-2-amino-4-oxy-pyrimidine) results in a modified nucleotide which will not effectively base pair with guanosine but will form a base pair with isoguanosine. Isocytosin e is available from Sigma Chemical Co. (St. Louis, Mo.); isocytidine may be prepared by the method described by Switzer et al. (1993) Biochemistry 32:10489-10496 and references cited therein; 2'-deoxy-5-methyl-isocytidine may be prepared by the method of Tor et al. (1993) J. Am. Chem. Soc. 115:4461-4467 and references cited therein; and isoguanine nucleotides may be prepared using the method described by Switzer et al. (1993), supra, and Mantsch et al. (1993) Biochem. 14:5593-5601, or by the method described U.S. Pat. No. 5,780,610 to Collins et al. The non-natural base pairs referred to as κ and π., may be synthesized by the method described in Piccirilli et al. (1990) Nature 343:33-37 for the synthesis of 2,6-diaminopyrimidine and its complement (1-methylpyrazolo [4,3]-pyrimidine-5,7-(4H,6H)-dione. Other such modified nucleotidic units which form unique base pairs have been described in Leach et al. (1992) J. Am. Chem. Soc. 114:3675-3683 and Switzer et al., supra, or will be apparent to those of ordinary skill in the art.

Preferably, the set of amplification primers comprises at least one, two, three, or four, or more primers and/or probes that contain a universal base. As used herein, the term "universal base" refers to a nucleotide analog that can hybridize to more than one nucleotide selected from A, T, C, and G. In some embodiments, the universal base can be selected from the group consisting of deoxyinosine, 3-nitropyrrole, 4-nitroindole, 6-nitroindole, 5-nitroindole. Preferably, the universal base is deoxyinosine. In some embodiments, the set of amplification primers, and probes disclosed herein include at least one primer and/or probe that has one, two, three, four, five, six, seven, eight, nine, ten, or more universal bases.

The primers and/or probes are preferably between 10 and 45 nucleotides in length. For example, the primers and or probes can be at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or more nucleotides in length. Primers and/or probes can be provided in any suitable form, included bound to a solid support, liquid, and lyophilized, for example. In some embodiments, the primers and/or probes include oligonucleotides that hybridize to a target nucleic acid sequence over the entire length of the oligonucleotide sequence. Such sequences can be referred to as "fully complementary" with respect to each other. Where an oligonucleotide is referred to as "substantially complementary" with respect to a nucleic acid sequence herein, the two sequences can be fully complementary, or they may form mismatches upon hybridization, but retain the ability to hybridize under stringent conditions or standard PCR conditions as discussed below. As used herein, the term "standard PCR conditions" include, for example, any of the PCR conditions disclosed herein, or known in the art, as described in, for example, PCR 1: A Practical Approach, M. J. McPherson, P. Quirke, and G. R. Taylor, Ed., (c) 2001, Oxford University Press, Oxford, England, and PCR Protocols: Current Methods and Applications, B. White, Ed., (c) 1993, Humana Press, Totowa, N.J.

As used herein, the term "substantially complementary" refers to the complementarity between two nucleic acids, e.g., the complementary region of the capture probe and the target sequence, and/or between the linker sequence of the capture probe and the complementary region of the competitor nucleic acid. The complementarity need not be perfect; there may be any number of base pair mismatches that between the two nucleic acids. However, if the number of mutations is so great that no hybridization can occur under even the least stringent of hybridization conditions, the sequence is not a substantially complementary sequence. When two sequences are referred to as "substantially complementary" herein, it is meant that the sequences are sufficiently complementary to the each other to hybridize under the selected reaction conditions. The relationship of nucleic acid complementarity and stringency of hybridization sufficient to achieve specificity is well known in the art and described further below in reference to sequence identity, melting temperature and hybridization conditions. Therefore, substantially complementary sequences can be used in any of the detection methods described herein. Such probes can be, for example, perfectly complementary or can contain from 1 to many mismatches so long as the hybridization conditions are sufficient to allow, for example discrimination between a target sequence and a non-target sequence. Accordingly, substantially complementary sequences can refer to sequences ranging in percent identity from 100, 99, 98, 97, 96, 95, 94, 93, 92, 91, 90, 89, 85, 80, 75 or less, or any number in between, compared to the reference sequence.

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

Primer Pairs

In some embodiments, the set of amplification primers includes one or more, e.g., 1, 2, 3, 4, 5, 6, 7, 8, 9, 10, 11, 12, 13, 14, 15, or more primer pairs. As used herein, the term "primer pair" can refer to two primers that individually hybridize to opposite strands of a target nucleic acid, e.g., an ESBL-encoding nucleic acid, e.g., a CTX-M gene or fragment thereof, or the like, wherein each primer can be extended at its 3' end to form a target amplification product, for example in a polymerase chain reaction (PCR). Primer pairs can include forward and reverse primers.

In some embodiments, the compositions and methods disclosed herein include a primer pair that comprises at least one set of amplification primers that hybridize to a CTX-M gene. For example, the compositions and methods disclosed herein can be used to detect and/or identify CTX-M beta-lactamases from a bacteria listed in Table 1. In some embodiments, the compositions and methods include a plurality of amplification primers, that collectively enable the detection and identification CTX-M beta lactamases from all of the bacteria listed in Table 1. In some embodiments, the compositions and method disclosed herein include primer pairs that collectively hybridize to and amplify nucleic acids of CTX-M nucleic acids from at least two CTX-M groups selected from CTX-M-1, CTX-M-2, CTX-M-8, CTX-M-9 and CTX-M-25. Primers useful for the detection and identification of CTX-M-1 include, for example, oligonucleotides that have at least 10 consecutive nucleotides of SEQ ID NOs: 1, 2, 5, 11, 12, 13, 14, 32, and 33 or the complements thereof, or that are substantially complementary to, and/or hybridize under stringent conditions to SEQ ID NOs:1, 2, 5, 11, 12, 13, 14, 32, and 33 or the complements thereof.

Primers useful for the detection and identification of CTX-M-2 include oligonucleotides that have at least 10 consecutive nucleic acids of SEQ ID NOs: 3, 4, 5, 15, 16, 17 18, 32 and 33, or the complements thereof, or that are substantially complementary to, and/or hybridize under stringent conditions to SEQ ID NOs: 3, 4, 5, 15, 16, 17 18, 32 and 33, or the complements thereof. Primers useful for the detection and identification of CTX-M-8 include oligonucleotides that have at least 10 consecutive nucleic acids of SEQ ID NOs: 6, 7, 10, 19, 20, 21, 22, 27, 28, and 31, or the complements thereof, or that are substantially complementary to, and/or hybridize under stringent conditions to SEQ ID NOs: 3, 4, 5, 15, 16, 17 18, 32 and 33, or the complements thereof. Primers useful for the detection and identification of CTX-M-9 include oligonucleotides that have at least 10 consecutive nucleic acids of SEQ ID NOs: 8, 9, 10, 23, 24, 25, 26, 29, 30, and 31, or the complements thereof, or that are substantially complementary to, and/or hybridize under stringent conditions to SEQ ID NOs: 8, 9, 10, 23, 24, 25, 26, 29, 30, and 31, or the complements thereof. The skilled artisan will appreciate that some embodiments include any combination of the primer pairs disclosed herein, e.g., any combination of primer pairs of SEQ ID NOs: 1 and 2, SEQ ID NOs: 3 and 4, SEQ ID NOs: 6 and 7, SEQ ID NOs: 8 and 9, SEQ ID NOs: 27 and 28, and SEQ ID NOs: 29 and 30. In some embodiments, the compositions and methods include primers and probes consisting of, consisting essentially of, or comprising SEQ ID NOs: 1-10, or having at least 10, 11, 12, 13, 14, 15, or more, consecutive nucleotides of SEQ ID NOs: 1-10, or that are substantially complementary to, and hybridize under stringent conditions to SEQ ID NOs: 1-10 or the complement thereof. In some embodiments, the compositions and methods include primers and probes consisting of, consisting essentially of, or comprising SEQ ID NOs: 1-5 and 27-31, or having at least 10, 11, 12, 13, 14, 15, or more, consecutive nucleotides of comprising SEQ ID NOs: 1-5 and 27-31, or that are substantially complementary to, and hybridize under stringent conditions to SEQ ID NOs: 1-5 and 27-31 or the complement thereof.

In some embodiments, the compositions and methods include primers and or probes for the detection and/or identification of additional sequences, including, for example, for the detection of a carbapenemase gene, e.g., as disclosed in PCT Publication No. WO 08/124,670. In some embodiments, the compositions and methods disclosed herein include primers having at least ten consecutive nucleotides of SEQ ID NOs: 34 and 35, or the complements thereof. In some embodiments, the compositions and methods disclosed herein include primers having at least ten consecutive nucleotides of SEQ ID NOs: 37 and 38, or the complements thereof. In some embodiments, the compositions and methods disclosed herein include primers that are substantially complementary to, and/or that hybridize under stringent conditions to the sequences of SEQ ID NOs: 34 and 35 or the complements thereof. In some embodiments, the compositions and methods disclosed herein include primers that are substantially complementary to, and/or that hybridize under stringent conditions to the sequences of SEQ ID NOs: 37 and 38 or the complements thereof.

In some embodiments disclosed herein, the compositions and/or methods can include one or more primers, wherein the primers include at least 8, 9, 10, 11, 12, 13, 14, 15, 16, 17, 18, 19, 20, 21, 22, 23, 24, 25, or more consecutive nucleic acids of the sequences of SEQ ID NO's:1-22, or the complement thereof.

TABLE 2

PRIMERS/PROBES

| SEQ ID NO: | Primer Name | Sequence |
|---|---|---|
| 1 | ctxm1-616F | CYGCTTCCTGGGTTGTGG |
| 2 | ctxm1-740R | TTGRGGCTGGGTGAAGTAAG |
| 3 | ctxm2-609F | GGTMTGCCGAAATSWTGG |
| 4 | ctxm2-776R | CGCAGCCAGAAHATCCCGAC |
| 5 | ctxm1/2-657B | ccagcgTATGGYACCACCAACGATAT CGCGGcgctgg |
| 6 | ctxm8-7F | TGTRTGCSCAGGCGAACG |
| 7 | ctxm8-119R | GTAGAGCGTCTGTGYGTTATCG |
| 8 | ctxm9-7F | TTTATGCGCAGACGAGTG |
| 9 | ctxm9-117R | AAAGCACCTGCGTATTATCT |
| 10 | ctxm8/9-42B | cgaggcGCGGCGCTGGARAAAAGCAGg cctcg |
| 11 | ctxm1-599F | GYATTCAGGCWGGACTGCC |
| 12 | ctxm1-633F | GGGGGATAAACCGGCAG |

TABLE 2-continued

PRIMERS/PROBES

| SEQ ID NO: | Primer Name | Sequence |
|---|---|---|
| 13 | ctxm1-756R | GCTTTCTGCCTTAGGTTGRG |
| 14 | ctxm1-723R | ARTGACCAGAATCAGCGGC |
| 15 | ctxm2-590F | TAGCGCGAGCATTCRGGC |
| 16 | ctxm2-624F | TGGGKAGTGGGCGATAAA |
| 17 | ctxm2-791R | TACGATTTTCGCCGCCGCAG |
| 18 | ctxm2-759R | GACGGYTTTCCGCCTTCT |
| 19 | ctxm8-1F | YGCCGCTGTRTGCSCAGGC |
| 20 | ctxm8-22F | ACGAYGTTCARCAAAAGC |
| 21 | ctxm8-131R | CTCRTCGGCGCGGTAGAGC |
| 22 | ctxm8-102R | TATCGGCGGTGTYAATCARCG |
| 23 | ctxm9-1F | CRMCGCTTTATGCGCAGAC |
| 24 | ctxm9-21F | ARTGCGGKGCARCAAAAG |
| 25 | ctxm9-102R | TATCTKYGGTATCGATGAGC |
| 26 | ctxm9-132R | GTTCATCACCGCGATAAAGC |
| 27 | ctxm8-146F | CAGCACCAGTAARGTGATG |
| 28 | ctxm8-256R | TTGTAGTTAAYCARGTCYGARG |
| 29 | ctxm9-122F | CGGTGATGAACGCTTTCC |
| 30 | ctxm9-242R | ATCGGCAGGCTTGATCTC |
| 31 | ctxm8/9-183B | cggcgatAAGCARAGTGAAACGCAAAAGatcgccg |
| 32 | ctxm1/2-664T-LNA | cCaCcaAcgaTatcgCg |
| 33 | ctxm1/2-659T | TGGYACCACCAACGATATCGCGGT |
| 34 | KPC-2F | AACTGACACTGGGCTCTG |
| 35 | KPC-2R | ATACMCTCCGCAGGTTCC |
| 36 | KPC-2B | cgcgatcACACGACCGGCAACCACCGCAgatcgcg |
| 37 | KPC-3F | GATRGATACCGGCTCAGG |
| 38 | KPC-3R | GTAACGGATGGGTGTGTC |
| 39 | KPC-3B | cgcgatcGCTGCCGCTGTGCTGGCTCGgatcgcg |
| 40 | CTXMI-F3 | GACGATGTCACTGGCTGAGC |
| 41 | CTXM1-R2 | AGCCGCCGACGCTAATACA |
| 42 | TOHO1-2F | GCGACCTGGTTAACTACAATCC |
| 43 | THOH1-1R | CGGTAGTATTGCCCTTAAGCC |
| 44 | CTXM825F | CGCTTTGCCATGTGCAGCACC |
| 45 | CTXM825R | GCTCAGTACGATCGAGCC |
| 46 | CTXM914F | GCTGGAGAAAAGCAGCGGAG |
| 47 | CTXM914R | GTAAGCTGACGCAACGTCTG |

Probes

In some embodiments, the probe can include a detectable label. Labels of interest include directly detectable and indirectly detectable radioactive or non-radioactive labels such as fluorescent dyes. Directly detectable labels are those labels that provide a directly detectable signal without interaction with one or more additional chemical agents. Examples of directly detectable labels include fluorescent labels. Indirectly detectable labels are those labels which interact with one or more additional members to provide a detectable signal. In this latter embodiment, the label is a member of a signal producing system that includes two or more chemical agents that work together to provide the detectable signal. Examples of indirectly detectable labels include biotin or digoxigenin, which can be detected by a suitable antibody coupled to a fluorochrome or enzyme, such as alkaline phosphatase. In many preferred embodiments, the label is a directly detectable label. Directly detectable labels of particular interest include fluorescent labels. Fluorescent labels that find use in the embodiments disclosed herein include a fluorophore moiety. Specific fluorescent dyes of interest include: xanthene dyes, e.g., fluorescein and rhodamine dyes, such as fluorescein isothiocyanate (FITC), 2-[ethylamino)-3-(ethylimino)-2-7-dimethyl-3H-xanthen-9-yl]benzoic acid ethyl ester monohydrochloride (R6G)(emits a response radiation in the wavelength that ranges from about 500 to 560 nm), 1,1,3,3,3',3'-Hexamethylindodicarbocyanine iodide (HIDC) (emits a response radiation in the wavelength that ranged from about 600 to 660 nm), 6-carboxyfluorescein (commonly known by the abbreviations FAM and F), 6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R),5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g., umbelliferone; benzamide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3 (emits a response radiation in the wavelength that ranges from about 540 to 580 nm), Cy5 (emits a response radiation in the wavelength that ranges from about 640 to 680 nm), etc; BODIPY dyes and quinoline dyes. Specific fluorophores of interest include: Pyrene, Coumarin, Diethylaminocoumarin, FAM, Fluorescein Chlorotriazinyl, Fluorescein, R110, Eosin, JOE, R6G, HIDC, Tetramethylrhodamine, TAMRA, Lissamine, ROX, Napthofluorescein, Texas Red, Napthofluorescein, SYBR green, Cy3, and Cy5, and the like.

In preferred embodiments, the compositions and methods disclosed herein include a molecular beacon probe, a TAQMAN™ probe, or a SCORPION™ probe. For example, in some embodiments, the compositions and methods disclosed herein include one or more molecular beacon probes, wherein the probes comprise the sequence of SEQ ID NO:5, 10, 31, 32, or 33, e.g., a probe as shown in any one of SEQ ID NO:25, 26, 27, 28, 32, and/or 33:

```
ccagcgTATGGYACCACCAACGATATCGCGGc    (SEQ ID NO: 5)
gctgg cgaggcGCGGCGCTGGARAAAAGCAGgcctcg    (SEQ ID NO: 10)

cgcgatcACACGACCGGCAACCACCGCAgatcgcg (SEQ ID NO: 36)
```

-continued

| | |
|---|---|
| cgcgatcGCTGCCGCTGTGCTGGCTCGgatcgcg | (SEQ ID NO: 39) |
| cggcgatAAGCARAGTGAAACGCAAAAGatcgccg | (SEQ ID NO: 31) |
| cCaCcaAcgaTatcgCg | (SEQ ID NO: 32) |
| TGGYACCACCAACGATATCGCGGT | (SEQ ID NO: 33) |

In some embodiments, the probes, e.g., SEQ ID NOs: 25-28 and 32-33, are labeled using an FAM fluorophore quenching molecule and a DABCYL quencher. In some embodiments, the probes are TAQMAN™ probes, molecular beacon probes, or SCORPION™ probes. In some embodiments, the one or more of the amplification primers can be labeled, e.g., with a fluorescent moiety, such as SYBR green, or the like.

The primer and probe sequences disclosed herein can be modified to include additional nucleotides at the 5' or the 3' terminus Likewise, in some embodiments, the primer and probe sequences can be modified by having nucleotides substituted within the sequence. It is recognized that the primer and probe sequences must contain enough complementarity to hybridize specifically to the respective target nucleic acid sequence. In this manner, at least 1, 2, 3, 4, or up to about 5 nucleotides can be substituted.

SEQ ID NO 32 and 33 are both specific to the CTX-M clusters 1 and 2 In some embodiments, the probe SEQ ID NO 32 can contain five locked nucleic acids (LNA). In some embodiments SEQ ID NO:33 is a TAQMAN™ probe. In some embodiments, SEQ ID NO 33 contains one or more degenerate bases, and specifically anneals (e.g., under stringent hybridization conditions and/or standard PCR conditions) to both CTX-M 1 and CTX-M 2.

Chemical synthesis methods that can be used to make the primers of the embodiments disclosed herein, include, but are not limited to, the phosphotriester method described by Narang et al. (1979) Methods in Enzymology 68:90, the phosphodiester method disclosed by Brown et al. (1979) Methods in Enzymology 68:109, the diethylphosphoramidate method disclosed by Beaucage et al. (1981) Tetrahedron Letters 22:1859, and the solid support method described in U.S. Pat. No. 4,458,066.

The use of an automated oligonucleotide synthesizer to prepare synthetic oligonucleotide primers of the embodiments disclosed herein is also contemplated.

Annealing and Specific Binding

In some embodiments, binding or annealing of the primers and/or probes to target nucleic acid sequences is accomplished through hybridization. It will be appreciated by one skilled in the art that specific hybridization is achieved by selecting sequences which are at least substantially complementary to the target or reference nucleic acid sequence. This includes base-pairing of the oligonucleotide target nucleic acid sequence over the entire length of the oligonucleotide sequence. Such sequences can be referred to as "fully complementary" with respect to each other. Where an oligonucleotide is referred to as "substantially complementary" with respect to a nucleic acid sequence herein, the two sequences can be fully complementary, or they may form mismatches upon hybridization, but retain the ability to hybridize under stringent conditions or standard PCR conditions as discussed below.

In some embodiments, the sample or specimen is contacted with a set of amplification primers and a probe. Preferably, the amplification primers and probes hybridize to target nucleic acids under a single set of conditions, i.e., stringent conditions, including standard PCR conditions discussed below. As used herein, the term "stringent conditions" Stringent hybridization conditions can vary (for example from salt concentrations of less than about 1 M, more usually less than about 500 mM and preferably less than about 200 mM) and hybridization temperatures can range (for example, from as low as 0° C. to greater than 22° C., greater than about 30° C. and (most often) in excess of about 37° C. depending upon the lengths and/or the nucleic acid composition of the probes. Longer fragments may require higher hybridization temperatures for specific hybridization. As several factors affect the stringency of hybridization, the combination of parameters is more important than the absolute measure of a single factor. Accordingly, by way of example, the term "stringent hybridization conditions" can refer to either or both of the following: a) 6×SSC at about 45° C., followed by one or more washes in 0.2×SSC, 0.1% SDS at 65° C., and b) 400 mM NaCl, 40 mM PIPES pH 6.4, 1 mM EDTA, 50° C. or 70° C. for 12-16 hours, followed by washing. In some embodiments, the term "stringent conditions" can refer to standard PCR conditions.

In some embodiments, the sample or specimen is contacted with a set of amplification primers under standard PCR conditions. For a review of PCR technology, including standard PCR conditions, applied to clinical microbiology, see DNA Methods in Clinical Microbiology, Singleton P., published by Dordrecht; Boston: Kluwer Academic, (2000) Molecular Cloning to Genetic Engineering White, B. A. Ed. in *Methods in Molecular Biology* 67: Humana Press, Totowa (1997) and "PCR Methods and Applications", from 1991 to 1995 (Cold Spring Harbor Laboratory Press). Non-limiting examples of "PCR conditions" include the conditions disclosed in the references cited herein, such as, for example, 50 mM KCl, 10 mM Tris-HCl (pH 9.0), 0.1% Triton X-100, 2.5 mM $MgCl_2$, with an annealing temperature of 72° C.; or 4 mM $MgCl_2$, 100 mM Tris, pH 8.3, 10 mM KCl, 5 mM $(NH_4)_2SO_4$, 0.15 mg BSA, 4% Trehalose, with an annealing temperature of 59° C., or 50 mM KCl, 10 mM Tris-HCl (pH 9.0), 0.1% Triton X-100, 2.5 mM $MgCl_2$, with an annealing temperature of 55° C., or the like.

In some embodiments, the methods disclosed herein comprise a PCR, for example, QPCR, based method of amplification and detection of ESBLs, such as CTX-M nucleic acids, using the primers and probes described herein. In various embodiments, the methods disclosed herein are capable of detecting the presence of ESBLs, such as CTX-Ms at a concentration of bacteria that is within physiological ranges (i.e., the concentration of bacteria in a sample collected from a subject infected with the bacteria). Thus, a sample can be directly screened without the need for isolating, concentrating, or expanding (e.g., culturing) the bacterial population in order to detect the presence of an ESBL, e.g., a CTX-M. In various embodiments, the methods disclosed herein are capable of detecting the presence of an ESBL from a sample that has a concentration of bacteria of about 1×103 CFU/ml, about 1×104 CFU/ml, about 1×105 CFU/ml, or about 1×106 CFU/ml.

Numerous different PCR or QPCR protocols are known in the art and exemplified herein below and can be directly applied or adapted for use using the presently described compositions for the detection of ESBLs, including CTX-Ms in a sample.

Generally, in PCR, a target polynucleotide sequence is amplified by reaction with at least one oligonucleotide primer or pair of oligonucleotide primers. The primer(s) hybridize to a complementary region of the target nucleic acid and a DNA polymerase extends the primer(s) to amplify the target sequence. Under conditions sufficient to provide polymerase-based nucleic acid amplification products, a nucleic acid fragment of one size dominates the reaction products (the target polynucleotide sequence that is the amplification product). The amplification cycle is repeated to increase the concentration of the single target polynucleotide sequence. The reaction can be performed in any thermocycler commonly used for PCR. However, preferred are cyclers with real-time fluorescence measurement capabilities, for example, SMARTCYCLER® (Cepheid, Sunnyvale, Calif.), ABI PRISM 7700® (Applied Biosystems, Foster City, Calif.), ROTOR-GENE™; (Corbett Research, Sydney, Australia), LIGHTCYCLER® (Roche Diagnostics Corp, Indianapolis, Ind.), ICYCLER® (Biorad Laboratories, Hercules, Calif.) and MX4000® (Stratagene, La Jolla, Calif.

Some embodiments provide methods including Quantitative PCR (QPCR) (also referred as real-time PCR). QPCR can provide quantitative measurements, and also provide the benefits of reduced time and contamination. As used herein, "quantitative PCR" (or "real time QPCR") refers to the direct monitoring of the progress of a PCR amplification as it is occurring without the need for repeated sampling of the reaction products. In QPCR, the reaction products may be monitored via a signaling mechanism (e.g., fluorescence) as they are generated and are tracked after the signal rises above a background level but before the reaction reaches a plateau. The number of cycles required to achieve a detectable or "threshold" level of fluorescence (herein referred to as cycle threshold or "CT") varies directly with the concentration of amplifiable targets at the beginning of the PCR process, enabling a measure of signal intensity to provide a measure of the amount of target nucleic acid in a sample in real time.

In some embodiments, a labeled probe can be used to detect the extension product generated by PCR amplification. Any probe format utilizing a labeled probe comprising sequences disclosed herein can be used, e.g., SCORPION™ probes, sunrise probes, TAQMAN™ probes, or molecular beacon probes as is known in the art or described elsewhere herein. In some embodiments, the probes can be used at a concentration of about 0.01 µM, 0.02 µM, 0.03 µM, 0.04 µM, 0.05 µM, 0.06 µM, 0.07 µM, 0.08 µM, 0.09 µM, 0.1 µM, 0.11 µM, 0.12 µM, 0.13 µM, 0.14 µM, 0.15 µM, 0.16 µM, 0.17 µM, 0.18 µM, 0.19 µM, 0.2 µM, 0.21 µM, 0.22 µM, 0.23 µM, 0.24 µM, 0.25 µM, 0.26 µM, 0.27 µM, 0.28 µM, 0.29 µM, 0.3 µM, 0.31 µM, 0.32 µM, 0.33 µM, 0.34 µM, 0.35 µM, 0.36 µM, 0.37 µM, 0.38 µM, 0.39 µM, 0.4 µM, 0.42 µM, 0.46 µM, 0.48 µM, 0.5 µM, or more, or any concentration in between. In some embodiments, the reaction can include about 0.1 µM SEQ ID NO 32 and/or about 0.3 µM SEQ ID NO 33.

Methods for setting up a PCR reaction are well known to those skilled in the art. The reaction mixture minimally comprises template nucleic acid (except in the case of a negative control as described below) and oligonucleotide primers and/or probes in combination with suitable buffers, salts, and the like, and an appropriate concentration of a nucleic acid polymerase. As used herein, "nucleic acid polymerase" refers to an enzyme that catalyzes the polymerization of nucleoside triphosphates. Generally, the enzyme will initiate synthesis at the 3'-end of the primer annealed to the target sequence, and will proceed in the 5'-direction along the template until synthesis terminates. An appropriate concentration includes one that catalyzes this reaction in the presently described methods. Known DNA polymerases useful in the methods disclosed herein include, for example, *E. coli* DNA polymerase I, T7 DNA polymerase, *Thermus thermophilus* (Tth) DNA polymerase, *Bacillus stearothermophilus* DNA polymerase, *Thermococcus litoralis* DNA polymerase, *Thermus aquaticus* (Taq) DNA polymerase and *Pyrococcusfuriosus* (Pfu) DNA polymerase.

In addition to the above components, the reaction mixture of the present methods includes primers, probes, and deoxyribonucleoside triphosphates (dNTPs).

Usually the reaction mixture will further comprise four different types of dNTPs corresponding to the four naturally occurring nucleoside bases, i.e., dATP, dTTP, dCTP, and dGTP. In some of the embodiments disclosed herein, each dNTP will typically be present in an amount ranging from about 10 to 5000 µM, usually from about 20 to 1000 µM, about 100 to 800 µM, or about 300 to 600 µM.

The reaction mixture prepared in the first step of the methods of the embodiments disclosed herein further includes an aqueous buffer medium that includes a source of monovalent ions, a source of divalent cations, and a buffering agent. Any convenient source of monovalent ions, such as potassium chloride, potassium acetate, ammonium acetate, potassium glutamate, ammonium chloride, ammonium sulfate, and the like may be employed. The divalent cation may be magnesium, manganese, zinc, and the like, where the cation will typically be magnesium. Any convenient source of magnesium cation may be employed, including magnesium chloride, magnesium acetate, and the like. The amount of magnesium present in the buffer may range from 0.5 to 10 mM, and can range from about 1 to about 6 mM, or about 3 to about 5 mM. Representative buffering agents or salts that may be present in the buffer include Tris, Tricine, HEPES, MOPS, and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5, for example, about pH 6.0, 6.5, 7.0, 7.5, 8.0, 8.5, 9.0, or 9.5. Other agents that may be present in the buffer medium include chelating agents, such as EDTA, EGTA, and the like. In some embodiments, the reaction mixture can include BSA, or the like.

In preparing the reaction mixture, the various constituent components may be combined in any convenient order. For example, the buffer may be combined with primer, polymerase, and then template nucleic acid, or all of the various constituent components may be combined at the same time to produce the reaction mixture.

Alternatively, commercially available premixed reagents can be utilized in the methods disclosed herein according to the manufacturer's instructions, or modified to improve reaction conditions (e.g., modification of buffer concentration, cation concentration, or dNTP concentration, as necessary), including, for example, TAQMAN® Universal PCR Master Mix (Applied Biosystems), OMNIMIX® or SMARTMIX® (Cepheid), IQ™ Supermix (Bio-Rad Laboratories), LIGHTCYCLER® FastStart (Roche Applied Science, Indianapolis, Ind.), or BRILLIANT® QPCR Master Mix (Stratagene, La Jolla, Calif.).

Following preparation of the reaction mixture, the reaction mixture can be subjected to primer extension reaction conditions ("conditions sufficient to provide polymerase-based nucleic acid amplification products"), i.e., conditions that permit for polymerase-mediated primer extension by addition of nucleotides to the end of the primer molecule using the template strand as a template. In many embodiments, the primer extension reaction conditions are amplification conditions, which conditions include a plurality of reaction cycles, where each reaction cycle comprises: (1) a denaturation step, (2) an annealing step, and (3) a polymerization step. The number of reaction cycles will vary depending on the application being performed, but will usually be at least 15, more usually at least 20, and may be as high as 60 or higher, where the number of different cycles will typically range from about 20 to 40. For methods where more than about 25, usually more than about 30 cycles are performed, it may be convenient or desirable to introduce additional polymerase into the reaction mixture such that conditions suitable for enzymatic primer extension are maintained.

The denaturation step comprises heating the reaction mixture to an elevated temperature and maintaining the mixture at the elevated temperature for a period of time sufficient for any double-stranded or hybridized nucleic acid present in the reaction mixture to dissociate. For denaturation, the temperature of the reaction mixture will usually be raised to, and maintained at, a temperature ranging from about 85 to 1000 C., usually from about 90 to 98° C., and more usually from about 93 to 96° C., for a period of time ranging from about 3 to 120 sec, usually from about 3 sec.

Following denaturation, the reaction mixture will be subjected to conditions sufficient for primer annealing to template nucleic acid present in the mixture (if present), and for polymerization of nucleotides to the primer ends in a manner such that the primer is extended in a 5' to 3' direction using the nucleic acid to which it is hybridized as a template, i.e., conditions sufficient for enzymatic production of primer extension product. In this embodiment, the annealing and extension processes occur in the same step. The temperature to which the reaction mixture is lowered to achieve these conditions will usually be chosen to provide optimal efficiency and specificity, and will generally range from about 50 to 75° C., usually from about 55 to 70° C., and more usually from about 60 to 68° C., more particularly around 600 C. Annealing conditions will be maintained for a period of time ranging from about 15 sec to 30 min, usually from about 20 sec to 5 min, or about 30 sec to 1 minute, or about 30 seconds This step can optionally comprise one of each of an annealing step and an extension step with variation and optimization of the temperature and length of time for each step. In a two-step annealing and extension, the annealing step is allowed to proceed as above. Following annealing of primer to template nucleic acid, the reaction mixture will be further subjected to conditions sufficient to provide for polymerization of nucleotides to the primer ends as above. To achieve polymerization conditions, the temperature of the reaction mixture will typically be raised to or maintained at a temperature ranging from about 65 to 75° C., usually from about 67 to 73° C. and maintained for a period of time ranging from about 15 sec to 20 min, usually from about 30 sec to 5 min.

In some embodiments, the cycling can include a 15-minute initial denaturation at 95° C., which is performed only once, followed by a denaturation step at 95° C. for 1 second, and an annealing/elongation step at 60° C. for 25 seconds. This two-step cycle can be repeated multiple times, e.g., about 45 times. In some embodiments, a final elongation step can be added at 72° C. for 10 minutes.

In some embodiments, the cycling can include a 15-minute initial denaturation step at 95° C., is followed by multiple cycles (e.g., about 45 cycles) of: denaturation at 95° C. for 1 second, annealing at 60° C. for 9 seconds and elongation at 72° C. for 9 seconds. A final elongation step can be added of 72° C. for 10 minutes.

The above cycles of denaturation, annealing, and polymerization may be performed using an automated device, typically known as a thermal cycler. Thermal cyclers that may be employed are described elsewhere herein as well as in U.S. Pat. Nos. 5,612,473; 5,602,756; 5,538,871; and 5,475,610; the disclosures of which are herein incorporated by reference.

The methods disclosed herein can also be used in non-PCR based applications to detect a target nucleic acid sequence, where such target may be immobilized on a solid support. Methods of immobilizing a nucleic acid sequence on a solid support are known in the art and are described in Ausubel et ah, eds. (1995) Current Protocols in Molecular Biology (Greene Publishing and Wiley-Interscience, NY), and in protocols provided by the manufacturers, e.g., for membranes: Pall Corporation, Schleicher & amp; Schuell; for magnetic beads: Dynal; for culture plates: Costar, Nalgenunc; for bead array platforms: Luminex and Becton Dickinson; and, for other supports useful in the embodiments disclosed herein, CPG, Inc.

The person skilled in the art of nucleic acid amplification knows the existence of other rapid amplification procedures such as ligase chain reaction (LCR), transcription-based amplification systems (TAS), self-sustained sequence replication (3SR), nucleic acid sequence-based amplification (NASBA), strand displacement amplification (SDA) and branched DNA (bDNA) (Persing et al. (1993) Diagnostic Molecular Microbiology Principles and Applications (American Society for Microbiology, Washington, D.C.). The scope of the embodiments disclosed herein is not limited to the use of amplification by PCR, but rather includes the use of any rapid nucleic acid amplification methods or any other procedures that may be useful with the sequences of the embodiments disclosed herein for the detection and/or quantification of the ESBL antibiotic resistance gene(s), e.g., CTX-M genes.

Further, variations on the exact amounts of the various reagents and on the conditions for the PCR or other suitable amplification procedure (e.g., buffer conditions, cycling times, etc.) that lead to similar amplification or detection/quantification results are known to those of skill in the art and are considered to be equivalents. In one embodiment, the subject QPCR detection has a sensitivity of detecting fewer than 50 copies (preferably fewer than 25 copies, more preferably fewer than 15 copies, still more preferably fewer than 10 copies) of target nucleic acid (i.e., ESBL nucleic acids, including CTX-M genes) in a sample. In one embodiment, a hot-start PCR reaction is performed (e.g., using a hot start Taq DNA polymerase) so as to improve PCR reaction by decreasing background from non-specific amplification and to increase amplification of the desired extension product.

Controls

In some embodiments, the PCR or QPCR reactions disclosed herein can contain various controls. Such controls can include a "no template" negative control, in which primers, buffer, enzyme(s) and other necessary reagents (e.g., magnesium chloride, nucleotides) are cycled in the absence of added test sample. A positive control including a known target nucleic acid can also be run in parallel. In some embodiments, both a positive control and negative control can be included in the amplification reaction. A single reaction may contain either a positive control, a negative control, or a sample template, or a single reaction may contain both a sample template and a positive control.

In addition to "no template" controls, negative controls can also include amplification reactions with non-specific target nucleic acid included in the reaction, or can be samples prepared using any or all steps of the sample preparation (from nucleic acid extraction to amplification preparation) without the addition of a test sample (e.g., each step uses either no test sample or a sample known to be free of ESBL's, such as CTX-M).

Positive and negative controls are useful for setting the parameters within which a test sample will be classified as having or not having an ESBL.

For example, in a QPCR reaction, the cycle threshold at which an ESBL, e.g., a CTX-M is detected in a positive control sample can be used to set the threshold for classifying a sample as "positive," and the cycle threshold at which the ESBL of interest, e.g., CTX-M is detected in a negative control sample can be used to set the threshold for classifying a sample as "negative." The CT from a single reaction may be used for each control, or the median or mean of replicate samples may be used. In yet another embodiment, historical control values may be used. The minimum level of detection for each of the negative and the positive controls is typically set at the lower end of the 95% confidence interval of the mean CT across multiple reactions. This value can be adjusted depending on the requirements of the diagnostic assay.

Preferably, PCR controls should be performed at the same time as the test sample, using the same reagents, in the same amplification reaction.

Some embodiments provide for the determination of the identity and or amount of target amplification products. The identity of the primer extension or amplification product can be confirmed using standard molecular techniques including (for example) a Southern blot assay. In a Southern blot assay, the amplification products are separated by electrophoresis, transferred to a membrane (i.e., nitrocellulose, nylon, etc.), reacted with an oligonucleotide probe or any portion of the nucleic acid sequence of interest. The probe is then modified to enable detection. The modification methods can be the incorporation of a radiolabeled nucleotide or any number of non-radioactive labels (such as biotin). The oligonucleotide probe used in the Southern blot assay is derived from the nucleic acid sequence and hence is specific for CTX-M nucleic acids, and can be a probe comprising the sequence set forth in SEQ ID NOs:5, 10 31, 32, and 33. The probe used in the Southern blot assay can be prepared using routine, standard methods. For example, the probe can be isolated, cloned, and restricted using routine techniques known in the art or can be made using the chemical synthesis methods described previously herein Alternatively, the amplification products can be detected using dot blot analysis. Dot blot analysis involves adhering an oligonucleotide probe (such as the one described previously) to a nitrocellulose or solid support such as, but not limited to, a bead (such as, but not limited to, polystyrene beads, magnetic beads, or non magnetic beads, etc.), walls of a reaction tray, strips (such as, but not limited to, nitrocellulose strips), a test tube. The sample containing the labeled amplification product is added, reacted, washed to removed unbound sample, and a labeled, amplified product attached to the probe is visualized using routine techniques known in the art. A more stringent way to verify the primer extension product or amplification product is through direct sequencing using techniques well known in the art Kits Also provided herein are "kits" containing the elements necessary to carry out the methods described herein. Such a kit can comprise a carrier being compartmentalized to receive in close confinement therein one or more containers, such as tubes or vials. One of the containers may contain at least one unlabeled or detectably labeled primer or probe disclosed herein. The primer or primers can be present in lyophilized form or in an appropriate buffer as necessary. One or more containers may contain one or more enzymes or reagents to be utilized in PCR reactions. These enzymes may be present by themselves or in admixtures, in lyophilized form or in appropriate buffers.

Finally, the kit can include all of the additional elements necessary to carry out the methods disclosed herein, such as buffers, extraction reagents, enzymes, pipettes, plates, nucleic acids, nucleoside triphosphates, filter paper, gel materials, transfer materials, autoradiography supplies, and the like.

Preferably, the kits include at least: (a) a labeled oligonucleotide, where the kit includes two or more distinguishable oligonucleotides, e.g., that hybridize to a nucleotide sequence encoding a EMBL, e.g., a CTX-M gene; and (b) instructions for using the provided labeled oligonucleotide(s) in a high fidelity amplification, e.g., PCR, reaction, such as QPCR. In one embodiment the two distinguishable oligonucleotides will be selected from the group consisting of SEQ ID NOS: 1-24.

In some embodiments, the kits include additional reagents that are required for or convenient and/or desirable to include in the reaction mixture prepared during the methods disclosed herein, where such reagents include: one or more polymerases; an aqueous buffer medium (either prepared or present in its constituent components, where one or more of the components may be premixed or all of the components may be separate), and the like. The various reagent components of the kits may be present in separate containers, or may all be precombined into a reagent mixture for combination with template nucleic acid.

In addition to the above components, in some embodiments, the kits can also include instructions for practicing the methods disclosed herein. These instructions can be present in the kits in a variety of forms, one or more of which may be present in the kit. One form in which these instructions can be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address that may be used via the internet to access the information at a removed site. Any convenient means may be present in the kits.

The disclosures of each of the following references are herein incorporated by reference in their entirety.

REFERENCES

1. Rasmussen and Bush. 1997. Carbapenem-Hydrolyzing β-Lactamases. *Antimicrob. Agents Chemother* 41: 223-232.
2. Woodford et al. 2004. Outbreak of *Klebsiella pneumoniae* Producing a New Carbapenem-Hydrolyzing Class A β-Lactamase, KPC-3, in a New York Medical Center. *Antimicrob. Agents Chemother* 48: 4793-4799.
3. Yigit et al. 2001. Novel Carbapenem-Hydrolyzing β-Lactamase, KPC-1, from a Carbapenem-Resistant Strain of *Klebsiella pneumoniae. Antimicrob. Agents Chemother* 45: 1151-1161.
4. *Manual of Microbiology*, $8^{th}$ edition. Edited by P R Murray, E J Baron, J H Jorgensen, M A Pfaller, and R H Yolken. ASM Press, Washington D.C., 2003.
5. Clinical and Laboratory Standard Institute. 2008. Performance Standards for Antimicrobial Susceptibility Testing; Eighteenth Informational Supplement M100-S18. Clinical and Laboratory Standard Institute, Wayne, Pa.

6. Dieffenbach & Dveksler. 2003. PCR Primer: A Laboratory Manual. CSHL Press, 520 p.
7. Devor, E. J. 2005. Locked Nucleic Acids (LNAs). *Molecular Genetics and Bioinformatics: Integrated DNA technologies*.

The invention described and claimed herein is not to be limited in scope by the specific embodiments herein disclosed, since these embodiments are intended as illustrations of several aspects of the invention. Any equivalent embodiments are intended within the scope of this invention. Indeed, various modifications of the embodiments in addition to those shown and described herein will become apparent to those skilled in the art from the foregoing description. The appended claims are intended to cover such modifications.

What is claimed is:

1. A composition for the detection and/or identification of CTX-M extended spectrum β-lactamase sequences comprising CTX-M isoforms 1-82 in a specimen, comprising:
    a set of amplification primers in solution,
        wherein the set of amplification primers comprises a plurality of amplification primer pairs comprising first and second primers,
        wherein said plurality of amplification primer pairs is collectively 100% complementary to each of CTX-M isoforms 1-82, and hybridizes to and produces target amplification products of any of CTX-M isoforms 1-82 when said any of CTX-M isoforms 1-82 are present in a specimen under conditions sufficient to provide polymerase-based nucleic acid-based amplification,
        wherein at least one primer comprises a nucleotide sequence selected from the group consisting of SEQ ID NOs: 1-4, 6, 7, 11, 13-16, 18-25, and 27-28, comprising at least one substitution of a naturally occurring nucleotide with a nucleotide analog that can hybridize to more than one nucleotide selected from A, T, C, and G;
    wherein said first and second primers in each amplification primer pair in said plurality of amplification primer pairs are 12 to 45 bases in length and comprise at least 12 consecutive nucleotides of at least one primer pair selected from the group consisting of:

SEQ ID NOs: 1 and 2 or the complements thereof;
SEQ ID NOs: 3 and 4 or the complements thereof;
SEQ ID NOs: 6 and 7 or the complements thereof;
SEQ ID NOs: 27 and 28 or the complements thereof;
SEQ ID NOs: 8 and 9 or the complements thereof; and
SEQ ID NOs: 29 and 30 or the complements thereof,
and wherein said first and second primers in each amplification primer pair in said plurality of amplification primer pairs are 100% complementary to at least one of SEQ ID NOs: 48-51 or the complement thereof.

2. The composition of claim 1, further comprising at least one probe that hybridizes to the target sequence.

3. The composition of claim 2, wherein said probe is selected from the group consisting of a molecular beacon probe, a TAQMAN™ fluorescent probe, and a scorpion fluorescent probe.

4. The composition of claim 2, further comprising at least one probe that can hybridize to the target amplification products from at least two CTX-M group target amplification products under standard PCR conditions.

5. The composition of claim 2, further comprising one or more probes, wherein said one or more probes can collectively hybridize to the target amplification products from CTX-M groups CTX-M-1, CTX-M-2, CTX-M-8, CTX-M-9, and CTX-M-25, under standard PCR conditions.

6. The composition of claim 1, further comprising at least one probe, wherein said at least one probe comprises at least 12 consecutive nucleotides selected from the group consisting of: SEQ ID NO:5, SEQ ID NO:10, SEQ ID NO:31, SEQ ID NO:32, and SEQ ID NO:33.

7. The composition of claim 1, wherein said set of amplification primers comprises:
CYGCTTCCTGGGTTGTGG (SEQ ID NO:1) or the complement thereof;
TTGRGGCTGGGTGAAGTAAG (SEQ ID NO:2) or the complement thereof;
GGTMTGCCGAAATSWTGG (SEQ ID NO:3) or the complement thereof;
CGCAGCCAGAAHATCCCGAC (SEQ ID NO:4) or the complement thereof;
TGTRTGCSCAGGCGAACG (SEQ ID NO:6) or the complement thereof, or CAGCACCAGTAARGTGATG (SEQ ID NO:27) or the complement thereof;
GTAGAGCGTCTGTGYGTTATCG (SEQ ID NO:7) or the complement thereof, or TTGTAGTTAAYCARGTCYGARG (SEQ ID NO:28) or the complement thereof;
TTTATGCGCAGACGAGTG (SEQ ID NO:8) or the complement thereof, or CGGTGATGAACGCTTTCC (SEQ ID NO:29) or the complement thereof; and
AAAGCACCTGCGTATTATCT (SEQ ID NO:9) or the complement thereof, or ATCGGCAGGCTTGATCTC (SEQ ID NO:30) or the complement thereof.

8. The composition of claim 7, further comprising at least one probe, wherein said at least one probe comprises at least 12 consecutive nucleotides selected from the group consisting of: SEQ ID NO:5, SEQ ID NO:10, SEQ ID NO:31, SEQ ID NO:32, and SEQ ID NO:33.

9. The composition of claim 1, further comprising an amplification primer pair that hybridizes to nucleic acids flanking a target sequence within or including part of a carbapenamase gene.

10. The composition of claim 8, wherein at least one probe comprises SEQ ID NO: 32, or the complement thereof, and wherein said probe comprises at least five locked nucleic acids.

11. The composition of claim 1, wherein said set of amplification primers comprises:
CYGCTTCCTGGGTTGTGG (SEQ ID NO:1) or the complement thereof;
TTGRGGCTGGGTGAAGTAAG (SEQ ID NO:2) or the complement thereof;
GGTMTGCCGAAATSWTGG (SEQ ID NO:3) or the complement thereof;
CGCAGCCAGAAHATCCCGAC (SEQ ID NO:4) or the complement thereof;
TGTRTGCSCAGGCGAACG (SEQ ID NO:6) or the complement thereof;
GTAGAGCGTCTGTGYGTTATCG (SEQ ID NO:7) or the complement thereof;
TTTATGCGCAGACGAGTG (SEQ ID NO:8) or the complement thereof; and AAAGCACCTGCGTATTATCT (SEQ ID NO:9) or the complement thereof.

12. The composition of claim 1, wherein said set of amplification primers comprises:
CYGCTTCCTGGGTTGTGG (SEQ ID NO:1) or the complement thereof;
TTGRGGCTGGGTGAAGTAAG (SEQ ID NO:2) or the complement thereof;
GGTMTGCCGAAATSWTGG (SEQ ID NO:3) or the complement thereof;
CGCAGCCAGAAHATCCCGAC (SEQ ID NO:4) or the complement thereof;
CAGCACCAGTAARGTGATG (SEQ ID NO:27) or the complement thereof;
TTGTAGTTAAYCARGTCYGARG (SEQ ID NO:28) or the complement thereof;
CGGTGATGAACGCTTTCC (SEQ ID NO:29) or the complement thereof; and
ATCGGCAGGCTTGATCTC (SEQ ID NO:30) or the complement thereof.

13. The composition of claim 1, wherein said set of amplification primers comprises:
CYGCTTCCTGGGTTGTGG (SEQ ID NO:1) or the complement thereof;
TTGRGGCTGGGTGAAGTAAG (SEQ ID NO:2) or the complement thereof;
GGTMTGCCGAAATSWTGG (SEQ ID NO:3) or the complement thereof;
CGCAGCCAGAAHATCCCGAC (SEQ ID NO:4) or the complement thereof;
TGTRTGCSCAGGCGAACG (SEQ ID NO:6) or the complement thereof;
GTAGAGCGTCTGTGYGTTATCG (SEQ ID NO:7) or the complement thereof;
CGGTGATGAACGCTTTCC (SEQ ID NO:29) or the complement thereof; and
ATCGGCAGGCTTGATCTC (SEQ ID NO:30) or the complement thereof.

14. The composition of claim 1, wherein said set of amplification primers comprises:
CYGCTTCCTGGGTTGTGG (SEQ ID NO:1) or the complement thereof;
TTGRGGCTGGGTGAAGTAAG (SEQ ID NO:2) or the complement thereof;
GGTMTGCCGAAATSWTGG (SEQ ID NO:3) or the complement thereof;
CGCAGCCAGAAHATCCCGAC (SEQ ID NO:4) or the complement thereof;
CAGCACCAGTAARGTGATG (SEQ ID NO:27) or the complement thereof;
TTGTAGTTAAYCARGTCYGARG (SEQ ID NO:28) or the complement thereof;

TTTATGCGCAGACGAGTG (SEQ ID NO:8) or the complement thereof; and AAAGCACCTGCGTAT-TATCT (SEQ ID NO:9) or the complement thereof.

15. The composition of claim 1, wherein the at least one substitution of a naturally occurring nucleotide with a nucleotide analog that can hybridize to more than one nucleotide selected from A, T, C, and G is a substitution for a degenerate base in the sequence selected from the group consisting of SEQ ID NOs: 1-4, 6, 7, 11, 13-16, 18-25, and 27-28.

16. A method for detecting and or identifying CTX-M extended spectrum β-lactamase sequences comprising CTX-M isoforms 1-82 in a specimen, comprising:
    obtaining a sample from the specimen to be analyzed for the presence of CTX-M extended spectrum β-lactamase sequences comprising CTX-M isoforms 1-82;
    contacting the sample with the composition of claim 15 under conditions sufficient to provide polymerase-based nucleic acid amplification products,
    providing reagents and conditions for extension of the primers to generate the target amplification product; and
    determining the presence and/or amount of the target amplification products.

17. The method of claim 16, further comprising contacting said sample with at least one probe that hybridizes to at least one target amplification product.

18. The method of claim 16, wherein said set of amplification primers comprises a plurality of amplification primer pairs, wherein said plurality of amplification primer pairs collectively hybridize to, and produce target amplification products in the presence of, CTX-M nucleic acids from each of the bacterial strains listed in Table 1.

19. The method of claim 17, wherein said probe is selected from the group consisting of a molecular beacon probe, a TAQMAN™ fluorescent probe, and a scorpion fluorescent probe.

20. The method of claim 16, further comprising contacting said sample with one or more probes, wherein said one or more probes collectively hybridizes to the target amplification products from CTX-M groups CTX-M-1, CTX-M-2, CTX-M-8, CTX-M-9, and CTX-M-25, under said conditions sufficient to provide polymerase-based nucleic acid amplification products.

21. The method of claim 16, wherein said set of amplification primers comprises at least two primers, wherein each primer comprises at least 12 consecutive nucleotides selected from the group consisting of:
    CYGCTTCCTGGGTTGTGG (SEQ ID NO:1) or the complement thereof;
    TTGRGGCTGGGTGAAGTAAG (SEQ ID NO:2) or the complement thereof;
    GGTMTGCCGAAATSWTGG (SEQ ID NO:3) or the complement thereof;
    CGCAGCCAGAAHATCCCGAC (SEQ ID NO:4) or the complement thereof;
    TGTRTGCSCAGGCGAACG (SEQ ID NO:6) or the complement thereof;
    GTAGAGCGTCTGTGYGTTATCG (SEQ ID NO:7) or the complement thereof;
    TTTATGCGCAGACGAGTG (SEQ ID NO:8) or the complement thereof; and
    AAAGCACCTGCGTATTATCT (SEQ ID NO:9) or the complement thereof.

22. The method of claim 21, further comprising contacting said sample with at least one probe, wherein said at least one probe comprises at least 12 consecutive nucleotides selected from the group consisting of: SEQ ID NO:5, SEQ ID NO:10, SEQ ID NO:31, SEQ ID NO:32, and SEQ ID NO:33.

23. The method of claim 16, wherein said set of amplification primers comprises at least two primers, wherein each primer comprises at least 12 consecutive nucleotides selected from the group consisting of:
    CYGCTTCCTGGGTTGTGG (SEQ ID NO:1) or the complement thereof;
    TTGRGGCTGGGTGAAGTAAG (SEQ ID NO:2) or the complement thereof;
    GGTMTGCCGAAATSWTGG (SEQ ID NO:3) or the complement thereof;
    CGCAGCCAGAAHATCCCGAC (SEQ ID NO:4) or the complement thereof;
    CAGCACCAGTAARGTGATG (SEQ ID NO:27) or the complement thereof;
    TTGTAGTTAAYCARGTCYGARG (SEQ ID NO:28) or the complement thereof;
    CGGTGATGAACGCTTTCC (SEQ ID NO:29) or the complement thereof; and
    ATCGGCAGGCTTGATCTC (SEQ ID NO:30) or the complement thereof.

24. The method of claim 23, further comprising contacting said sample with at least one probe, wherein said at least one probe comprises at least 12 consecutive nucleotides selected from the group consisting of: SEQ ID NO:5, SEQ ID NO:10, SEQ ID NO:31, SEQ ID NO:32, and SEQ ID NO: 33.

* * * * *